United States Patent
Sloan (10) Patent No.: US 7,729,773 B2
(45) Date of Patent: Jun. 1, 2010

(54) NEURAL STIMULATION AND OPTICAL MONITORING SYSTEMS AND METHODS

(75) Inventor: Leif R. Sloan, Seattle, WA (US)

(73) Assignee: Advanced Neuromodualation Systems, Inc., Plano, TX (US)

( * ) Notice: Subject to any disclaimer, the term of this patent is extended or adjusted under 35 U.S.C. 154(b) by 270 days.

(21) Appl. No.: 11/583,349

(22) Filed: Oct. 18, 2006

(65) Prior Publication Data

US 2007/0100398 A1    May 3, 2007

Related U.S. Application Data

(60) Provisional application No. 60/728,650, filed on Oct. 19, 2005.

(51) Int. Cl.
*A61N 1/00* (2006.01)
(52) U.S. Cl. ............... 607/45; 607/3; 600/310
(58) Field of Classification Search ......... 600/300–372; 607/1–76
See application file for complete search history.

(56) References Cited

U.S. PATENT DOCUMENTS

| | | |
|---|---|---|
| 2,721,316 A | 10/1955 | Shaw |
| 3,628,193 A | 12/1971 | Collins |
| 3,650,276 A | 3/1972 | Burghele et al. |
| 3,918,461 A | 11/1975 | Cooper |
| 4,030,509 A | 6/1977 | Heilman et al. |
| 4,125,116 A | 11/1978 | Fischell |
| 4,140,133 A | 2/1979 | Kastrubin et al. |
| 4,214,804 A | 7/1980 | Little |
| 4,245,645 A | 1/1981 | Picard et al. |
| 4,328,813 A | 5/1982 | Ray |
| 4,340,038 A | 7/1982 | McKean |

(Continued)

FOREIGN PATENT DOCUMENTS

DE    19750043    5/1999

(Continued)

OTHER PUBLICATIONS

Barr, Deborah et al., "Induction and Reversal of Long-Term Potentiation by Low-and High-Intensity Theta Pattern Stimulation," The Journal of Neuroscience, 15(7): pp. 5402-5410 (Jul. 1995).

(Continued)

*Primary Examiner*—Scott M Getzow
(74) *Attorney, Agent, or Firm*—Melissa Acosta; Christopher S. L. Crawford; Peter Lando (57) ABSTRACT

Neural stimulation and optical monitoring systems and methods are disclosed. In one embodiment, an apparatus for treating a neural condition includes a signal delivery device configured to be implanted into a patient proximate to a skull of the patient and positioned to apply electromagnetic signals to one or more target sites within the patient. The apparatus also includes an implantable optical monitoring assembly configured to monitor optical properties at one or more optical monitoring sites within the patient. The apparatus further includes a controller configured to be implanted into the patient. The controller is operatively coupled to the signal delivery device and the optical monitoring assembly and programmed to control both the signal delivery device and the optical monitoring assembly. The controller also includes a power source to power both the signal delivery device and the optical monitoring assembly.

3 Claims, 7 Drawing Sheets

U.S. PATENT DOCUMENTS

| | | | |
|---|---|---|---|
| 4,431,000 A | 2/1984 | Butler et al. | |
| 4,474,186 A | 10/1984 | Ledley et al. | |
| 4,542,752 A | 9/1985 | Dehaan et al. | |
| 4,590,946 A | 5/1986 | Loeb | |
| 4,607,639 A | 8/1986 | Tanagho et al. | |
| 4,646,744 A | 3/1987 | Capel | |
| 4,702,254 A | 10/1987 | Zabara | |
| 4,750,495 A | 6/1988 | Moore et al. | |
| 4,844,075 A | 7/1989 | Liss et al. | |
| 4,865,048 A | 9/1989 | Eckerson | |
| 4,869,255 A | 9/1989 | Putz | |
| 4,969,468 A | 11/1990 | Byers et al. | |
| 5,002,053 A | 3/1991 | Garcia-Rill et al. | |
| 5,024,226 A | 6/1991 | Tan | |
| 5,031,618 A | 7/1991 | Mullett | |
| 5,044,368 A | 9/1991 | Putz | |
| 5,054,906 A | 10/1991 | Lyons | |
| 5,063,932 A | 11/1991 | Dahl et al. | |
| 5,092,835 A | 3/1992 | Schurig et al. | |
| 5,121,754 A | 6/1992 | Mullett | |
| 5,125,888 A | 6/1992 | Howard et al. | |
| 5,143,089 A | 9/1992 | Alt | |
| 5,169,384 A | 12/1992 | Bosniak et al. | |
| 5,184,620 A | 2/1993 | Cudahy et al. | |
| 5,215,086 A | 6/1993 | Terry, Jr. et al. | |
| 5,217,013 A * | 6/1993 | Lewis et al. | 600/342 |
| 5,224,491 A | 7/1993 | Mehra | |
| 5,255,678 A | 10/1993 | Deslauriers et al. | |
| 5,263,967 A | 11/1993 | Lyons, III et al. | |
| 5,271,417 A | 12/1993 | Swanson et al. | |
| 5,282,468 A | 2/1994 | Klepinski | |
| 5,299,569 A | 4/1994 | Wernicke et al. | |
| 5,304,206 A | 4/1994 | Baker, Jr. et al. | |
| 5,314,458 A | 5/1994 | Najafi et al. | |
| 5,358,513 A | 10/1994 | Powell, III et al. | |
| 5,370,672 A | 12/1994 | Fowler et al. | |
| 5,405,375 A | 4/1995 | Ayers et al. | |
| 5,406,957 A | 4/1995 | Tansey | |
| 5,411,540 A | 5/1995 | Edell et al. | |
| 5,417,719 A | 5/1995 | Hull et al. | |
| 5,423,864 A | 6/1995 | Ljungstroem | |
| 5,464,446 A | 11/1995 | Dreessen et al. | |
| 5,520,190 A | 5/1996 | Benedict et al. | |
| 5,522,864 A | 6/1996 | Wallace et al. | |
| 5,537,512 A | 7/1996 | Hsia et al. | |
| 5,540,736 A | 7/1996 | Haimovish et al. | |
| 5,549,655 A | 8/1996 | Erickson | |
| 5,562,708 A | 10/1996 | Combs et al. | |
| 5,575,813 A | 11/1996 | Edell et al. | |
| 5,591,216 A | 1/1997 | Testerman et al. | |
| 5,593,432 A | 1/1997 | Crowther et al. | |
| 5,601,611 A | 2/1997 | Fayram et al. | |
| 5,601,835 A | 2/1997 | Sabel et al. | |
| 5,611,350 A | 3/1997 | John | |
| 5,628,317 A | 5/1997 | Starkebaum et al. | |
| 5,674,251 A | 10/1997 | Combs et al. | |
| 5,676,655 A | 10/1997 | Howard, III et al. | |
| 5,683,422 A | 11/1997 | Rise | |
| 5,702,429 A | 12/1997 | King | |
| 5,707,334 A | 1/1998 | Young | |
| 5,707,335 A | 1/1998 | Howard et al. | |
| 5,711,316 A | 1/1998 | Elsberry et al. | |
| 5,713,922 A | 2/1998 | King | |
| 5,713,923 A | 2/1998 | Ward et al. | |
| 5,716,377 A | 2/1998 | Rise et al. | |
| 5,722,401 A | 3/1998 | Pietroski | |
| 5,735,814 A | 4/1998 | Elsberry et al. | |
| 5,750,376 A | 5/1998 | Weiss et al. | |
| 5,752,979 A | 5/1998 | Benabid | |
| 5,769,778 A | 6/1998 | Abrams et al. | |
| 5,772,591 A | 6/1998 | Cram | |
| 5,782,798 A | 7/1998 | Rise | |
| 5,782,873 A | 7/1998 | Collins | |
| 5,792,186 A | 8/1998 | Rise | |
| 5,797,970 A | 8/1998 | Pouvreau | |
| 5,814,014 A | 9/1998 | Elsberry et al. | |
| 5,814,089 A | 9/1998 | Stokes et al. | |
| 5,814,092 A | 9/1998 | King | |
| 5,824,021 A | 10/1998 | Rise | |
| 5,824,030 A | 10/1998 | Yang et al. | |
| 5,832,932 A | 11/1998 | Elsberry et al. | |
| 5,833,603 A | 11/1998 | Kovacs et al. | |
| 5,833,709 A | 11/1998 | Rise et al. | |
| 5,843,148 A | 12/1998 | Gijsbers et al. | |
| 5,843,150 A | 12/1998 | Dreessen et al. | |
| 5,865,842 A | 2/1999 | Knuth et al. | |
| 5,885,976 A | 3/1999 | Sandyk | |
| 5,886,769 A | 3/1999 | Zolten | |
| 5,893,883 A | 4/1999 | Torgerson et al. | |
| 5,904,916 A | 5/1999 | Hirsh | |
| 5,913,882 A | 6/1999 | King | |
| 5,916,171 A | 6/1999 | Mayevsky | |
| 5,925,070 A | 7/1999 | King et al. | |
| 5,938,688 A | 8/1999 | Schiff | |
| 5,938,689 A | 8/1999 | Fischell et al. | |
| 5,941,906 A | 8/1999 | Barreras, Sr. et al. | |
| 5,964,794 A | 10/1999 | Bolz et al. | |
| 5,975,085 A | 11/1999 | Rise | |
| 5,978,702 A | 11/1999 | Ward et al. | |
| 5,983,140 A | 11/1999 | Smith et al. | |
| 6,006,124 A | 12/1999 | Fischell et al. | |
| 6,011,996 A | 1/2000 | Gielen et al. | |
| 6,016,449 A | 1/2000 | Fischell et al. | |
| 6,018,682 A | 1/2000 | Rise | |
| 6,021,352 A | 2/2000 | Christopherson et al. | |
| 6,026,326 A | 2/2000 | Bardy | |
| 6,035,236 A | 3/2000 | Jarding et al. | |
| 6,040,180 A | 3/2000 | Johe | |
| 6,042,579 A | 3/2000 | Elsberry et al. | |
| 6,052,624 A | 4/2000 | Mann | |
| 6,055,456 A | 4/2000 | Gerber | |
| 6,057,846 A | 5/2000 | Sever, Jr. | |
| 6,057,847 A | 5/2000 | Jenkins | |
| 6,058,331 A | 5/2000 | King | |
| 6,060,048 A | 5/2000 | Cherksey | |
| 6,061,593 A | 5/2000 | Fischell et al. | |
| 6,066,163 A | 5/2000 | John | |
| 6,094,598 A | 7/2000 | Elsberry et al. | |
| 6,095,148 A | 8/2000 | Shastri et al. | |
| 6,104,956 A | 8/2000 | Naritoku et al. | |
| 6,104,960 A | 8/2000 | Duysens et al. | |
| 6,122,548 A | 9/2000 | Starkebaum et al. | |
| 6,126,657 A | 10/2000 | Edwards et al. | |
| 6,128,537 A | 10/2000 | Rise | |
| 6,128,538 A | 10/2000 | Fischell et al. | |
| 6,132,361 A | 10/2000 | Epstein et al. | |
| 6,134,474 A | 10/2000 | Fischell et al. | |
| 6,152,143 A | 11/2000 | Edwards | |
| 6,161,044 A | 12/2000 | Silverstone | |
| 6,161,045 A | 12/2000 | Fischell et al. | |
| 6,176,242 B1 | 1/2001 | Rise | |
| 6,190,893 B1 | 2/2001 | Shastri et al. | |
| 6,198,958 B1 | 3/2001 | Ives et al. | |
| 6,205,360 B1 | 3/2001 | Carter et al. | |
| 6,210,417 B1 | 4/2001 | Baudino et al. | |
| 6,221,908 B1 | 4/2001 | Kilgard et al. | |
| 6,227,203 B1 | 5/2001 | Rise et al. | |
| 6,230,049 B1 | 5/2001 | Fischell et al. | |
| 6,233,480 B1 | 5/2001 | Hochman et al. | |
| 6,236,892 B1 | 5/2001 | Feler | |
| 6,246,912 B1 | 6/2001 | Sluijter et al. | |
| 6,248,126 B1 | 6/2001 | Lesser et al. | |
| 6,263,237 B1 | 7/2001 | Rise | |
| 6,280,462 B1 | 8/2001 | Hauser et al. | |

| | | | | | |
|---|---|---|---|---|---|
| 6,301,493 B1 | 10/2001 | Marro et al. | 2003/0074032 A1 | 4/2003 | Gliner |
| 6,319,241 B1 | 11/2001 | King et al. | 2003/0078633 A1 | 4/2003 | Firlik et al. |
| 6,339,725 B1 | 1/2002 | Naritoku et al. | 2003/0088274 A1 | 5/2003 | Gliner et al. |
| 6,353,754 B1 | 3/2002 | Fischell et al. | 2003/0097161 A1 | 5/2003 | Firlik et al. |
| 6,354,299 B1 | 3/2002 | Fischell et al. | 2003/0114886 A1 | 6/2003 | Gluckman et al. |
| 6,356,792 B1 | 3/2002 | Errico et al. | 2003/0125772 A1 | 7/2003 | Olsen et al. |
| 6,360,122 B1 | 3/2002 | Fischell et al. | 2003/0125786 A1 | 7/2003 | Gliner et al. |
| 6,366,813 B1 | 4/2002 | DiLorenzo | 2003/0130706 A1 | 7/2003 | Sheffield et al. |
| 6,375,666 B1 | 4/2002 | Mische | 2003/0149457 A1 | 8/2003 | Tcheng et al. |
| 6,405,079 B1 | 6/2002 | Ansarinia | 2003/0153959 A1 | 8/2003 | Thacker et al. |
| 6,418,344 B1 | 7/2002 | Rezai | 2003/0176901 A1 | 9/2003 | May |
| 6,427,086 B1 | 7/2002 | Fischell et al. | 2003/0181954 A1 | 9/2003 | Rezai |
| 6,456,886 B1 | 9/2002 | Howard, III et al. | 2003/0187490 A1 | 10/2003 | Gliner |
| 6,459,936 B2 | 10/2002 | Fischell et al. | 2003/0187491 A1 | 10/2003 | Greenberg et al. |
| 6,463,328 B1 | 10/2002 | John | 2003/0199741 A1* | 10/2003 | Martinez ................ 600/309 |
| 6,464,356 B1 | 10/2002 | Sabel et al. | 2004/0010290 A1* | 1/2004 | Schroeppel et al. ............ 607/3 |
| 6,466,822 B1 | 10/2002 | Pless | 2004/0030258 A1* | 2/2004 | Williams et al. ............ 600/544 |
| 6,473,639 B1 | 10/2002 | Fischell et al. | 2004/0073270 A1 | 4/2004 | Firlik et al. |
| 6,480,743 B1 | 11/2002 | Kirkpatrick et al. | 2004/0082847 A1 | 4/2004 | McDermott |
| 6,484,059 B2 | 11/2002 | Gielen | 2004/0088024 A1 | 5/2004 | Firlik et al. |
| 6,487,450 B1 | 11/2002 | Chen | 2004/0092809 A1 | 5/2004 | DeCharms |
| 6,497,699 B1 | 12/2002 | Ludvig et al. | 2004/0102828 A1 | 5/2004 | Lowry et al. |
| 6,499,488 B1 | 12/2002 | Hunter et al. | 2004/0111127 A1 | 6/2004 | Gliner et al. |
| 6,505,075 B1 | 1/2003 | Weiner | 2004/0127942 A1 | 7/2004 | Yomotov et al. |
| 6,507,755 B1 | 1/2003 | Gozani et al. | 2004/0131998 A1 | 7/2004 | Marom et al. |
| 6,529,774 B1 | 3/2003 | Greene | 2004/0138550 A1 | 7/2004 | Hartlep et al. |
| 6,532,387 B1* | 3/2003 | Marchitto et al. ............ 604/21 | 2004/0158298 A1 | 8/2004 | Gliner et al. |
| 6,556,868 B2 | 4/2003 | Naritoku et al. | 2004/0176831 A1 | 9/2004 | Gliner et al. |
| 6,569,654 B2 | 5/2003 | Shastri et al. | 2004/0181263 A1 | 9/2004 | Balzer et al. |
| 6,591,138 B1 | 7/2003 | Fischell et al. | 2004/0215287 A1 | 10/2004 | Swoyer et al. |
| 6,597,954 B1 | 7/2003 | Pless et al. | 2004/0236388 A1 | 11/2004 | Gielen et al. |
| 6,615,065 B1 | 9/2003 | Barrett et al. | 2004/0243205 A1 | 12/2004 | Keravel et al. |
| 6,622,048 B1 | 9/2003 | Mann et al. | 2004/0249422 A1 | 12/2004 | Gliner et al. |
| 6,633,780 B1 | 10/2003 | Berger | 2005/0004620 A1 | 1/2005 | Singhal et al. |
| 6,665,562 B2 | 12/2003 | Gluckman et al. | 2005/0015129 A1 | 1/2005 | Mische |
| 6,684,105 B2 | 1/2004 | Cohen et al. | 2005/0021104 A1 | 1/2005 | DiLorenzo |
| 6,687,525 B2 | 2/2004 | Llinas et al. | 2005/0021105 A1 | 1/2005 | Firlik et al. |
| 6,690,974 B2 | 2/2004 | Archer et al. | 2005/0021106 A1 | 1/2005 | Firlik et al. |
| 6,708,064 B2 | 3/2004 | Rezai | 2005/0021107 A1 | 1/2005 | Firlik et al. |
| 6,725,094 B2 | 4/2004 | Saberski | 2005/0021118 A1 | 1/2005 | Genau et al. |
| 6,735,474 B1 | 5/2004 | Loeb et al. | 2005/0033378 A1 | 2/2005 | Sheffield et al. |
| 6,764,498 B2 | 7/2004 | Mische | 2005/0033379 A1 | 2/2005 | Lozano et al. |
| 6,782,292 B2 | 8/2004 | Whitehurst | 2005/0070971 A1 | 3/2005 | Fowler et al. |
| 6,788,975 B1 | 9/2004 | Whitehurst et al. | 2005/0075679 A1 | 4/2005 | Gliner et al. |
| 6,795,737 B2 | 9/2004 | Gielen et al. | 2005/0075680 A1 | 4/2005 | Lowry et al. |
| 6,810,286 B2 | 10/2004 | Donovan et al. | 2005/0096701 A1 | 5/2005 | Donovan et al. |
| 6,839,594 B2 | 1/2005 | Cohen et al. | 2005/0113882 A1 | 5/2005 | Cameron et al. |
| 6,873,872 B2 | 3/2005 | Gluckman et al. | 2005/0119712 A1 | 6/2005 | Shafer |
| 6,882,881 B1 | 4/2005 | Lesser et al. | 2005/0154425 A1 | 7/2005 | Boveja et al. |
| 6,892,097 B2 | 5/2005 | Holsheimer | 2005/0154426 A1 | 7/2005 | Boveja et al. |
| 6,895,280 B2 | 5/2005 | Meadows et al. | 2005/0182453 A1 | 8/2005 | Whitehurst |
| 6,898,464 B2 | 5/2005 | Edell et al. | 2005/0203366 A1 | 9/2005 | Donoghue et al. |
| 6,907,296 B1 | 6/2005 | Doan et al. | 2005/0228451 A1 | 10/2005 | Jaax et al. |
| 6,934,580 B1 | 8/2005 | Osorio et al. | 2006/0004422 A1 | 1/2006 | De Ridder |
| 6,944,497 B2 | 9/2005 | Stypulkowski | 2006/0015153 A1 | 1/2006 | Gliner et al. |
| 6,944,501 B1 | 9/2005 | Pless | 2006/0106430 A1 | 5/2006 | Fowler et al. |
| 6,959,215 B2 | 10/2005 | Gliner et al. | 2006/0106431 A1 | 5/2006 | Wyler et al. |
| 6,990,377 B2 | 1/2006 | Gliner et al. | 2006/0129205 A1 | 6/2006 | Boveja et al. |
| 7,006,859 B1 | 2/2006 | Osorio et al. | 2006/0173522 A1 | 8/2006 | Osorio |
| 7,010,351 B2 | 3/2006 | Firlik et al. | 2006/0217782 A1 | 9/2006 | Boveja et al. |
| 7,024,247 B2 | 4/2006 | Gliner et al. | 2006/0241717 A1 | 10/2006 | Whitehurst et al. |
| 7,107,097 B2 | 9/2006 | Stern et al. | 2007/0027500 A1 | 2/2007 | Maschino et al. |
| 7,110,820 B2 | 9/2006 | Tcheng et al. | 2007/0032834 A1 | 2/2007 | Gliner et al. |
| 7,346,395 B2 | 3/2008 | Lozano et al. | 2007/0038264 A1* | 2/2007 | Jaax et al. ................ 607/45 |
| 7,353,065 B2* | 4/2008 | Morrell ........................ 607/45 | 2007/0055320 A1 | 3/2007 | Weinand |
| 2002/0062143 A1 | 5/2002 | Baudino et al. | 2007/0060974 A1 | 3/2007 | Lozano |
| 2002/0077670 A1 | 6/2002 | Archer | 2007/0088403 A1 | 4/2007 | Wyler et al. |
| 2002/0087201 A1 | 7/2002 | Firlik et al. | 2007/0088404 A1 | 4/2007 | Wyler et al. |
| 2002/0091419 A1 | 7/2002 | Firlik | 2007/0179534 A1 | 8/2007 | Firlik et al. |
| 2002/0099295 A1 | 7/2002 | Gil et al. | 2007/0179558 A1 | 8/2007 | Gliner et al. |
| 2002/0099412 A1 | 7/2002 | Fischell et al. | 2007/0288072 A1 | 12/2007 | Pascual-Leone et al. |
| 2002/0169485 A1 | 11/2002 | Pless et al. | 2008/0039895 A1 | 2/2008 | Fowler et al. |
| 2003/0028072 A1 | 2/2003 | Fischell et al. | 2008/0045775 A1 | 2/2008 | Lozano |

| | | |
|---|---|---|
| 2008/0139870 A1 | 6/2008 | Gliner et al. |
| 2008/0249591 A1 | 10/2008 | Gaw et al. |

FOREIGN PATENT DOCUMENTS

| | | |
|---|---|---|
| EP | 0319844 | 6/1989 |
| EP | 0314937 B1 | 12/1995 |
| EP | 0 998 958 | 5/2000 |
| EP | 1145736 | 10/2001 |
| EP | 1180056 | 11/2003 |
| WO | WO 87-07511 | 12/1987 |
| WO | WO 94-07564 | 4/1994 |
| WO | WO 95-21591 | 8/1995 |
| WO | WO 98-06342 | 2/1998 |
| WO | WO 01-97906 | 12/2001 |
| WO | WO 02-09811 | 2/2002 |
| WO | WO 02-36003 | 5/2002 |
| WO | WO 02-38031 | 5/2002 |
| WO | WO 02-38217 | 5/2002 |
| WO | WO-02-072194 | 9/2002 |
| WO | WO-03-026739 | 4/2003 |
| WO | WO-03-035163 | 5/2003 |
| WO | WO 03-043690 | 5/2003 |
| WO | WO 03-082402 | 10/2003 |
| WO | 03101532 A2 | 12/2003 |

OTHER PUBLICATIONS

Barres et al., "Proliferation of oligodendrocyte precursor cells depends on electrical activity in axons," Nature; Medical Research Council Developmental Neurobiology Programme, Department of Biology, University College, London, p. 258-260, (Jan. 21, 1993).

Behrens, T. et al., "Non-invasive mapping of connections between human thalamus and cortex using diffusion imaging," Nature neuroscience, vol. 6 No. 7, pp. 750-757 (Jul. 2003).

Bel, S. and Bauer, B.L., "Dorsal Column Stimulation (DCS): Cost to Benefit Analysis," Acta Neurochirurgica, Suppl. 52, pp. 121-123 (1991).

Benabid, A. L. et al., "Chronic electrical stimulation of the ventralis intermedius nucleus of the thalamus as a treatment of movement disorders," J. Neurosurg., Apr. 1997, 86(4); 737; http:—www.ncbi.nlm.nih.gov; [accessed Nov. 18, 2003].

Bezard et al., "Cortical Stimulation and Epileptic Seizure: A Study of the Potential Risk in Primates," Neurosurgery, vol. 45, No. 2, Aug. 1999, 346-350.

Binder, J. M.D., "Functional Magnetic Resonance Imaging: Language Mapping," Neurosurgery Clinics of North America, vol. 8, No. 3, Jul. 1997, pp. 383-392.

Bluestone, Avraham Y. et al., "Three-dimensional optical tomography of hemodynamics in the human head," Optics Express, vol. 9, No. 6, pp. 272-286 (Sep. 10, 2001).

Bozkurt et al., "A portable near infrared spectroscopy system for bedside monitoring of newborn brain," BioMedical Engineering OnLine 2005, 4:29, pp. 1-11.

Brain Electrical Stimulation to Enhance Recovery After Stroke, ClinicalTrials.gov, URL: http://www.clinicaltrials.gov/ct/show/NCT00085657?order=2 [Retrieved on Dec. 22, 2005].

Burnett, Mark G. et al., "Diffuse optical measurement of blood flow, blood oxygenation, and metabolism in a human brain during sensorimotor cortex activation," Optics Letters, vol. 29, No. 15, pp. 1766-1768 (Aug. 1, 2004).

Bury, Scott et al., "The Effects of Behavioral Demand on Motor Cortical and Cerebellar Structural Plasticity After Brain Injury in Adult Rats," http://www.mcmaster.ca-inabis98-schallert-bury0827-two.html#introduction, 2 pages [Retrieved on Mar. 1, 2003].

Butefisch et al., "Mechanisms of use-dependent plasticity in the human motor cortex," Proc. Natl. Acad. Sci. USA, vol. 97, No. 7, pp. 3661-3665 (Mar. 2000).

Canavero, S. and Paolotti, R., "Extradural Motor Cortex Stimulation for Advanced Parkinson's Disease: Case Report," Movement Disorders, 15(1):169-171, 2000.

Cao, Yue et al., "Cortical Language Activation in Stroke Patients Recovering From Aphasia With Functional MRI," Stroke, vol. 30, pp. 2331-2340, Nov. 1999.

Chance et al., "A novel method for fast imaging of brain function, non-invasively, with light," Optics Express, vol. 2, No. 10, May 1998, pp. 411-423.

Cheun et al., "Differentiation of a Stem Cell Line Toward a Neuronal Phenotype," Int. J. Devl. Neuroscience, vol. 9, No. 4, pp. 391-404 (1991).

Cicinelli et al., "Transcranial magnetic stimulation reveals an interhemispheric asymmetry of cortical inhibition in focal epilepsy," Neurophysiology, vol. 11, No. 4 Mar. 20, 2000, pp. 701-707.

Cincotta et al, "Reorganization of the motor cortex in a patient with congenital hemiparesis and mirror movements," Neurology, vol. 55, pp. 129-131 (2000).

Cincotta et al., "Suprathreshold 0.3 Hz repetitive TMS prolongs the cortical silent period: potential implications for therapeutic trials in epilepsy," Clinical Neurophysiology, vol. 114, 2003, pp. 1827-1833, Elsevier Ireland Ltd.

Classen et al., "Rapid Plasticity of Human Cortical Movement Representation Induced by Practice," The Journal of Neurophysiology, vol. 79, No. 2, pp. 1117-1123 (Feb. 1998).

Cohen et al., "Studies of Neuroplasticity With Transcranial Magnetic Stimulation," The Journal of Clinical Neurophysiology, vol. 15, No. 4 (1998).

Cramer et al., "Use of Functional MRI to Guide Decisions in a clinical Stroke Trial," Stroke, Journal of the American Heart Association, May 2005, pp. e50-e52, American Heart Association, Dallas TX.

Cramer, S.C. and Bastings, E.P., "Mapping clinically relevant plasticity after stroke," Neuropharmacology vol. 19, No. 5, pp. 842-851 (Apr. 2000).

Cytokines Web Clinical Significance, Cytokines Web, 2 pages, URL: http:—cmbi.bjmu.edu.cn-cmbidata-cgf-CGF_Database-cytweb-roles-index.html [Retrieved on Sep. 2, 2005].

Dam et al., "Effects of Fluoxetine and Maprotiline on Functional Recovery in Poststroke Hemiplegic Patients Undergoing Rehabilitation Therapy," Stroke, vol. 27, No. 7, pp. 1211-1214 (Jul. 1996).

De Ridder, Dirk et al., "Magnetic and electrical stimulation of the auditory cortex for intractable tinnitus," Journal Neurosurg., vol. 100, pp. 560-564, (Mar. 2004).

Di Lazzaro, V. et al., "Theta-burst repetitive transcranial magnetic stimulation suppresses specific excitatory circuits in the human motor cortex," Physiology in Press; published online on Apr. 21, 2005 as 10.1113-jphysiol.2005.087288.

Ding, Yuemin et al., "Neural Plasticity After Spinal Cord Injury," Current Pharmaceutical Design vol. 11, No. 11, pp. 1441-1450, Abstract Only, 1 page (Apr. 2005).

Duncan, Pamela W. et al., "Defining post-stroke recovery: implications for design and interpretation of drug trials," Neuropharmacology vol. 39, pp. 835-841 (2000).

Ferrari, A. et al., "Immature human NT2 cells grafted into mouse brain differentiate into neuronal and glial cell types," FEBS Letters, Dec. 8, 2000, pp. 121-125, vol. 486, No. 2, Elsevier Science B.V., Amsterdam.

Feys et al., "Value of somatosensory and motor evoked potentials in predicting arm recovery after a stroke," (Oct. 1999).

Franzini et al., "Reversal of thalamic hand syndrome by long-term motor cortex stimulation," Journal of Neurosurgery 93:873-875 (2000).

Fregni et al., "Antiepileptic Effects of Repetitive Transcranial Magnetic Stimulation in Patients with Cortical Malformations: An EEG and Clinical Study," ASSFN Proceedings 2004, Stereotactic and Functional Neurosurgery, 2005, 83:57-62.

Fregni, Felipe et al., "Anodal Transcranial Direct Current Stimulation of Prefrontal Cortex Enchances Working Memory," Experimental Brain Research vol. 166, No. 1, pp. 23-30 (Sep. 2005).

Gladstone et al., "Enhancing Recovery after Stroke with Noradrenergic Pharmacotherapy: A New Frontier?," Can J. Neurol. Sci., vol. 27, No. 2 (May 2000).

Gordon et al., "Parameters for direct cortical electrical stimulation in the human: histopathologic confirmation," Electroencephalography and clinical Neurophysiology, vol. 75, pp. 371-377 (1990).

Hagemann, Georg et al., "Increased Long-Term Potentiation in the Surround of Experimentally Induced Focal Cortical Infarction," Annals of Neurology, vol. 44, No. 2, pp. 255-258 (Aug. 1998).

Haglund, Michael M. et al., "Optical imaging of epileptiform and functional activity in human cerebral cortex," Nature, Aug. 20, 1992, pp. 668-671, vol. 358, Nature Publishing Group.

Hayakawa, Toshiji et al., "Changes in Cerebral Oxygenation and Hemodynamics During Obstructive Sleep Apneas," Chest, vol. 109, pp. 916-921 (1996).

Higurashi et al., "An Integrated Laser Blood Flowmeter," Journal of Lightwave Technology, vol. 21, No. 3, Mar. 2003, pp. 1-5.

Hodge, JR., C.J. and Boakye, M., "Biological Plasticity: The Future of Science in Neurosurgery," Neurosurgery, vol. 48, No. 1 (Jan. 2001).

Hoshi, Yoko et al., "Detection of dynamic changes in cerebral oxygenation coupled to neuronal function during mental work in a man," Neuroscience Letters, vol. 150, pp. 5-8 (1993).

Hoshino et al., "Application of multichannel near-infrared spectroscopic topography to physiological monitoring of the cortex during cortical mapping: technical case report," Surgical Neurology, vol. 64, pp. 272-275 (2005).

How Imagent™ Works. ISS Inc., http://www.iss.com-Products-imagent_fmri.html, 1 page [Retrieved on Oct. 14, 2005].

Huang, Ying-Zu et al., "Theta Burst Stimulation of the Human Motor Cortex," Neuron, vol. 45, pp. 201-206 (Jan. 20, 2005).

Hummel, Friedhelm et al., "Effects of non-invasive cortical stimulation on skilled motor function in chronic stroke," Brain Advance Access, pp. 1-10, (Jan. 5, 2005).

Imagent™ Functional Brain Imaging System, ISS, Inc., http://www.iss.com-Products-imagent.html, 2 pages [Retrieved on Oct. 14, 2005].

Imagent™ functional Near Infrared Imaging System (fNIRS) Brain Imaging Using Infrared Photons, ISS Inc., http://www.iss.com-products-imagent-Imagent.pdf, 8 pages [Retrieved on Oct. 14, 2005].

Ishibashi, Tomoko et al., "Astrocytes Promote Myelination in Response to Electrical Impulses," Neuron 49, pp. 823-832, (Mar. 16, 2006).

Janicek, Milos J. et al., "Dynamic Infrared Imaging of Newly Diagnosed Malignant Lymphoma Compared with Gallium-67 and Fluorine-18 Fluorodeoxyglucose (FDG) Positron Emission Tomography," Technology in Cancer Research and Treatment, vol. 2, No. 6, pp. 571-577 (Dec. 2003).

Kauhanen et al., "Domains and Determinants of Quality of Life After Stroke Caused by Brian Infarction," Arch. Phys. Med. Rehabil., vol. 81, pp. 1541-1546 (Dec. 2000).

Kelly-Spratt, K. "Transfection of PC-12 cells: a model system for primary neuronal cells," Qiagen News, Customer application article, www.qiagen.com, Issue 4, 1998, 2 pages.

Keyvani, Kathy et al., "Suppression of proteasome C2 contralateral to ischemic lesions in rat brain," Brain Research, vol. 858, pp. 386-392, 2000.

Kilgard, Michael et al., "Cortical Map Reorganization Enabled by Nucleus Basalis Activity," Science, vol. 279 pp. 1714-1717 (Mar. 13, 1998).

Kimura, K. et al., "Electrically induced neurite outgrowth of PC12 cells on the electrode surface," Entrez PubMed, http://www.ncbi.nlm.nih.gov/entrez/query.fcgi?db=pubmed&cmd=Retrieve&dopt=Abstract, 1 page.

Kinoshita et al., "Electric cortical stimulation suppresses epileptic and background activities in neocortical epilepsy and mesial temporal lobe epilepsy," Clinical Neurophysiology, vol. 116, 2005, pp. 1291-1299, Elsevier Ireland Ltd.

Kopell et al., "The Continuing Evolution of Psychiatric Neurosurgery," CNS Spectrums, vol. 5, No. 10, pp. 20-31 (Oct. 2000).

Kossoff et al., "Effect of an External Responsive Neurostimulator on Seizures and Electrographic Discharges during Subdural Electrode Monitoring," Epilepsia 45(12):1560-1567, 2004, Blackwell Publishing, Inc.

Lang, Nicolas et al., "Preconditioning with Transcranial Direct Current Stimulation Sensitizes the Motor Cortex to Rapid-Rate Transcranial Magnetic Stimulation and Controls the Direction of After-Effects," Biol Psychiatry 2004:56:634-639, 2004 Society of Biological Psychiatry.

Larson, John et al., "Reversal of LTP by theta frequency stimulation," Brain Research, 600: pp. 97-102 (1993).

Lazar, M. et al., "White Matter Tractography Using Diffusion Tensor Deflection," Human Brain Mapping, 18:306-321, (2003).

L-DOPA dyskinesias, BioChemistry of PD, http://www.mayo.edu-fdp-pd-info-dyskinesias.htm [Retrieved on Dec. 22, 2005].

Levy et al., "Functional MRI Evidence of Cortical Reorganization in Upper-Limb Stroke Hemiplegia Treated with Constraint-Induced Movement Therapy," American Journal of Physical Medicine & Rehabilitation, vol. 80, No. 1, pp. 4-7 (2001).

Liepert et al., "Treatment-Induced Cortical Reorganization After Stroke in Humans," Stroke, 31:1210-1216 (2000).

Lutsep et al., "Safety of Cortical Stimulation in Patients with Hemiparetic Stroke," Oasis, Online Abstract Submission and Invitation System—Program Planner, International Stroke Conference 2005, 1 pages, American Stroke Association.

Malenka, R.C. and Nicoll, R.A., "Long-Term Potenetiation—A Decade of Progress?," Neuroscience, vol. 285, No. 5435, Issue of Sep. 17, 1999, pp. 1870-1874.

Mansur, C.G. et al., "A sham stimulation-controlled trial of rTMS of the unaffected hemisphere in stroke patients," Neurology, vol. 64, pp. 1802-1804 (2005).

Martin et al., "Transcranial Magnetic Stimulation as a Complementary Treatment for Aphasia," Semin Speech Language, vol. 25, pp. 181-191 (2004) Abstract Only- 1 page.

Martinez et al., "Motor hand recovery after stroke Prognostic yield of early transcranial magnetic stimulation," Electromyography. Clin. Neurophysiology, vol. 39, pp. 405-410 (1999).

Meyerson, B.A. et al., "Motor Cortex Stimulation as Treatment of Trigeminal Neuropathic Pain", Acta Neurochirurgica Supplementum, vol. 58, pp. 150-153 (1993).

Misawa et al., "Low-frequency transcranial magnetic stimulation for epilepsia partialis continua due to cortical dysplasia," Journal of the Neurological Sciences, vol. 234, 2005, pp. 37-39.

Motamedi et al., "Optimizing Parameters for Terminating Cortical Afterdischarges with Pulse Stimulation," Epilepsia 43(8):836-846, 2002, Blackwell Publishing, Inc.

Netz et al., "Reorganization of motor output in the non-affected hemisphere after stroke," Brain, 120, pp. 1579-1586 (1997).

Nitsche, M.A. and Paulus, W., "Excitability changes induced in the human motor cortex by weak transcranial direct current stimulation," The Journal of Physiology, vol. 527.3, pp. 663-639 (2000).

Nitsche, Michael A. et al. "Facilitation of Implicit Motor Learning by Weak Transcranial Direct Current Stimulation of the Primary Motor Cortex in the Human," Journal of Cognitive Neuroscience 15:4, pp. 619-626, 2003 Massachusetts Institute of Technology.

Nitsche, Michael A. et al., "Level of action of cathodal DC opographyn induced inhibition of the human motor cortex," Dec. 2, 2002, Clinical Neurophysiology 114 (2003) 600-604.

Nudo, Randolph J. et al., "Recovery after damage to motor cortical areas," Current Opinion in Neurobiology, vol. 9, Issue 6, pp. 740-747, Dec. 1, 1999.

Oliveri et al., "Paired transcranial magnetic stimulation protocols reveal a pattern of inhibition and facilitation in the human parietal cortex," The Journal of Physiology, 529.2, pp. 461-468 (2000).

Panchanathan, Sethuraman et al., "Rehabilitation of patients with hemispatial neglect using visual-haptic feedback in Virtual reality environment," http://www.public.asu.edu-~tmcdani-publications.htm, 5 pages [Retrieved on Dec. 22, 2005].

Pascual-Leone et al., "Study and Modulation of Human Cortical Excitability With Transcranial Magnetic Stimulation," Journal of Clinical Neurophysiology, vol. 15, No. 4 (1998).

Pascual-Leone et al., "Transcranial magnetic stimulation and neuroplasticity," Neurophycologia 37, pp. 207-217 (1999).

Paulus, W, "Supplements to Clinical Neurophysiology," Transcranial Magnetic Stimulation and Transcranial Direct Current Stimulation (Supplements to Clinical Neurophysiology; vol. 56), pp. 249-254, 2003 Elsevier Science, B.V.

Paulus, Walter, "Toward Establishing a Therapeutic Window for rTMS by Theta Burst Stimulation," Neuron, vol. 45, pp. 181-183 (Jan. 20, 2005).

Penn, Michael, "Stemming Parkinson's," On Wisconsin Alumni Magazine, Summer 2003, http://www.uwalumni.com-onwisconsin-2003_summer-research.html, 1 page [Retrieved on Dec. 22, 2005].

Price, J. et al., "Neurotransplantation in neurodegenerative disease: a survey of relevant issues in developmental neurobiology," Novartis Foundation Symposium 231, 2000, pp. 148-165, Wiley, Chichester, UK.

Rezai, "Neurostimulation," Neurological Research, vol. 22, No. 3 pp. 235-273 (Apr. 2000).

Robinson, Kenneth R., "The Responses of Cells to Electrical Fields: A Review," The Journal of Cell Biology, vol. 101, pp. 2023-2027 (Dec. 1985).

Rossi et al., "Effects of Repetitive Transcranial Magnetic Stimulation on Movement-related Cortical Activity in Humans," Cerebral Cortex, vol. 10, No. 8, pp. 802-808 (Aug. 2000).

Roux et al., "Chronic Motor Cortex Stimulation for Phantom Limb Pain: A Functional Magnetic Resonance Imagining Study: Technical Cast Report," Neurosurgery, vol. 48, No. 3 (Mar. 2001).

Saitou et al., "Cerebral Blood Volume and Oxygenation Among Poststroke Hemiplegic Patients: Effects of 13 Rehabilitation Tasks Measured by Near-Infrared Spectroscopy," Arch. Phys. Med. Rehabil., vol. 81 pp. 1348-1356 (Oct. 2000).

Sandkuhler, "Learning and memory in pain pathways," Pain 88, pp. 113-118 (2000).

Sanes, "The Relation between Human Brain Activity and Hand Movements," NeuroImage 11, pp. 370-374 (2000).

Sanes, J. and Donoghue, J.P., "Plasticity and Primary Motor Cortex," Annual Review of Neuroscience 23:393-415 (2000).

Schaefer, Pamela W. et al., "Assessing Tissue Viability with MR Diffusion and Perfusion Imaging," AJNR, 24: pp. 436-443 (Mar. 2003).

Schiene, Klaus et al., "Neuronal Hyperexcitability and Reduction of GABA-Receptor Expression in the Surround of Cerebral Photothrombosis," Journal of Cerebral Blood Flow and Metabolism, vol. 16, No. 5, pp. 906-914 (1996).

Schiff et al., "A neuromodulation strategy for rational therapy of complex brain injury states," Neurological Research, vol. 22 pp. 267-272 (Apr. 2000).

SCIRun, Scientific Computing and Imaging Institute. http://www.sofware.sci.utah.edu-scirun.html, 2 pages [Retrieved on Jul. 24, 2005].

Shimizu et al., "Therapeutic efficacy of transcranial magnetic stimulation for hereditary spinocerebellar degeneration," Tohoku Journal of Experimental Medicine, 189(3):203-11 (Nov. 1999).

Shinohara et al., "Laser Doppler velocimeter using the self-mixing effect of a semiconductor laser diode," Applied Optics, vol. 25, No. 9, May 1986, p. 1417-1419.

Siebner et al., "Lasting cortical activation after repetitive TMS of the motor cortex," Neurology 54, pp. 956-963 (Feb. 2000).

Sioutos et al. Continuous Regional Cerebral Cortical Blood Flow Monitoring in Head-injured Patients, Neurosurgery, vol. 36, No. 5, May 1995, pp. 943-949.

Stefan et al., "Introduction of plasticity in the human motor cortex by paired associative stimulation," Brian, vol. 123, No. 3, pp. 572-584 (Mar. 2000).

Strangman, Gary et al., "A Quantitative Comparison of Simultaneous Bold fMRI and NIRS Recordings during Functional Brain Activation," NeuroImage, vol. 17, pp: 719-731 (2002).

Strangman, Gary et al., "Factors affecting the accuracy of near-infrared spectroscopy concentration calculations for focal changes in oxygenation parameters," NeuroImage, vol. 18, pp: 865-879 (2003).

Strangman, Gary et al., "Non-Invasive Neuroimaging Using Near-Infrared Light," Biological Psychiatry, vol. 52, pp: 679-693 (2002).

Strens, Lucy et al., "The Ipsilateral Human Motor Cortex Can Functionally Compensate for Acute Contralateral Motor Cortex Dysfunction," Current Biology, vol. 13, pp. 1201-1205 (Jul. 15, 2003).

Taga, Gentaro et al., "Brain imaging in awake infants by near-infrared optical topogrpahy," PNAS, vol. 100, No. 19, pp. 10722-10727 (Sep. 16, 2003).

Tang, Cha-Min et al., "Optical Coherence Tomography of the Human Basal Ganglion," Deep Brain Stimulation Consortium Meeting Program Book, Sep. 29-30, 2003, Washington DC.

The GES 250 for Dense-Array EEG Research, Electrical Geodesics, Inc., http://www.egi.com/ges250r_n.html, 3 pages [Retrieved on Aug. 25, 2005].

The INVOS Cerebral Oximeter, Somanetics, http://www.somanetics.net/invos.htm, 1 page [retrieved from the internet on Dec. 22, 2005].

The National Institutes of Health (NIH) Consensus Development Program, "Surgery for Epilepsy," National Institutes of Health Consensus Development conference Statement, Mar. 19-21, 1990, 16 pages.

Theoret, Hugo et al., "Exploring Paradoxical Functional Facilitation with TMS," Supplements to Clinical Neurophysiology, vol. 56, pp. 211-219 (2003).

Thomas, Carmen et al., "Do Children with aggressive behavior have temporal lobe changes?" Alasbimn Journal, Year 5, No. 19, 8 pages (Jan. 2003).

Timmermann, Lars et al., "The cerebral oscillatory network of parkinsonian resting tremor," Brain, vol. 126, pp. 199-212, (2003).

Toronov, Vlad et al., "Near-infrared study of fluctuations in cerebral hemodynamics during rest and motor stimulation: Temporal analysis and spatial mapping," Medical Physics, vol. 27, No. 4, pp. 801-815 (Apr. 2000).

Tractography, Absolute Astronomy Reference, http://www.absoluteastronomy.com-encyclopedia-T-Tr-Tractography.htm, 2 pages [Retrieved on Jul. 24, 2005].

Tsubokawa, T. et al., "Chronic Motor Cortex Stimulation for the Treatment of Central Pain," Acta Neurochirurgica, Supplementum. vol. 52, pp. 137-139 (1991).

Tsubokawa, T. et al., "Chronic Motor Cortex Stimulation in Patients with Thalamic Pain," J. Neurosurg 78:393-401, (Mar. 1993).

Tsubokawa, T. et al., "Treatment of Thalamic Pain by Chronic Motor Cortex Stimulation", PACE, vol. 14, pp. 131-134 (Jan. 1991).

Tuch, D. et al., "Conductivity Tensor Mapping of the Human Brain Using Diffusion Tensor MRI," Neurobiology, vol. 98 No. 20, pp. 11697-11701 (Sep. 25, 2001).

Turton et al., "Contralateral and ipsilateral EMG responses to transcranial magnetic stimulation during recovery of arm and hand function after stroke," Electroencephalography and Clinical Neurophysiology 101 pp. 316-328 (1996).

Turton, A. and Lemon, R.N., "The contribution of fast corticospinal input to the voluntary activation of proximal muscles in normal subjects and in stroke patients," Exp. Brain Res., vol. 129, pp. 559-572 (1999).

Van Der Lee et al., "The Infra- and Interrater Reliability of the Action Research Arm Test: A Practical Test of Upper Extremity Function in Patients With Stroke," Arch. Phys. Med. Rehabil., vol. 82 pp. 14-19 (Jan. 2001).

Velasco et al. "Absolute and Relative Predictor Values of Some Non-Invasive and Invasive Studies for the Outcome of Anterior Temporal Lobectormy," Science Direct, vol. 31, Issue 1, Jan.-Feb. 2000, pp. 62-74, Elsevier Science, Inc.

Velasco et al., "Acute and Chronic Electrical Stimulation of the Centromedian Thalamic Nucleus: Modulation of Reticulo-Cortical Systems and Predictor Factors for Generalized Seizure Control," Archives of Medical Research, vol. 31, 2000, pp. 304-315, Elsevier Science, Inc.

Velasco et al., "Electrical Stimulation for Epilepsy: Stimulation of Hippocampal Foci," Stereotactic and Functional Neurosurgery, vol. 77, 2001, pp. 223-227.

Velasco et al., "Subacute and Chronic Electrical Stimulation of the Hippocampus on Intractable Temporal Lobe Seizures: Preliminary Report," Archives of Medical Research, vol. 31, 2000, pp. 316-328, Elsevier Science, Inc.

Velasco et al., "Subacute Electrical Stimulation of the Hippocampus Blocks Intractable Temporal Lobe Seizures and Paroxysmal EEG Activities," Epilepsia, vol. 41, No. 2, 2000, pp. 158-169, Lippincott Williams & Wilkins, Philadelphia.

Walker-Batson et al., "Amphetamine Paired With Physical Therapy Accelerates Motor Recovery After Stroke," Stroke, vol. 26, No. 12, pp. 2254-2259 (1995).

Waxman et al., "The Interictal Behavior Syndrome of Temporal Lobe Epilepsy," Arch Gen Psychiatry, vol. 32, Dec. 1975, pp. 1580-1586.

Weinand et al., "Cerebral blood flow and temporal lobe epileptogenicity," J Neurosurg, vol. 86, Feb. 1997, pp. 226-232.

Weinand et al., "Cerebral blood flow and temporal lobe epileptogenicity," Neurosurgical Focus, Nov. 1996, vol. 1, No. 5, AANS.ORG, http://www.aans.org/education/journal/neurosurgical/nov96/1-5-3.asp, 17 pages.

Weinand et al., Long-term ictal monitoring with subdural strip electrodes: prognostic factors for selecting temporal lobectomy candidates, J Neurosurg, vol. 77, 1992, pp. 20-28.

Weinand et al., "Surface cortical cerebral blood flow monitoring and single photon emission computed tomography: prognostic factors for selecting temportal lobectormy candidates," Seizure, vol. 3, 1994, pp. 55-59.

Weinand et al., "Targeted Subthreshold Cortical Stimulation for Recovery of Motor Hand Function following Hemiparetic Stroke," Abstract: Apr. 18, 2005 AANS.org, http://www.aans.org/Library/Article.aspx?ArticleId=24934, 2 pages.

Weinand, Martin E. et al., "Cerebral blood flow and temporal lobe epileptogenicity," Retrieved from the Internet on Dec. 22, 2005, http://www.aans.org/education/journal/neurosurgical/nov96/1-5-3.asp, 13 pages.

Woodbury, D. et al., "Adult Rat and Human Bone Marrow Stromal Cells Differentiate Into Neurons," Journal of Neuroscience Research, 2000, vol. 61, pp. 364-370, Wiley Interscience, New York, NY.

Yamamoto et al., "Low-frequency Electric Cortical Stimulation Has an Inhibitory Effect on Epileptic Focus in Mesial Temporal Lobe Epilepsy," Epilepsia, vol. 43, No. 5, 2002, pp. 291-295, Blackwell Publishing, Inc.

Yokoh, Arika et al., "Intermittent versus continuous brain retraction," Journal of Neurosurgery, vol. 58, pp. 918-923 (Jun. 1983).

Ziemann et al., "Modulation of Plasticity in Human Motor Cortex after Forearm Ischemic Nerve Block," The Journal of Neuroscience 18(3):1115-1123 (Feb. 1998).

Delbello et al., "Magnetic Resonance Imaging Analysis of Amygdala and other Subcortical Brain Regions in Adolescents with Bipolar Disorders," Bipolar Disorders vol. 6, 2004, pp. 43-52.

Drevets at al., "Functional Anatomical Correlates of Antidepressants Drug Treatment Assessed Using PET Measures of Regional Glucose Metabolism," European Neuropsychopharmology vol. 12, 2002, pp. 527-544.

Fossati et al., "Neuroplasticity: from MRI to Depressive Symptoms," European Neuropsychophamacology vol. 14, 2004, pp. S503-S510.

Haldane et al., "New Insights Help Define the Pathophysiology of Bipolar Affective Disorder: Neuroimaging and Neuropathology Findings," Progress in Neuro-Psychopharmacology & Biological Psychiatry, vol. 28, 2004, pp. 943-960.

Keightley et al., "An fMRI study investigating cognitive modulation of brain regions associated with emotional processing of visual stimuli," Neuropsychologia, 41(5): 585-96, 2003.

Kennedy et al., "Changes in regional barin glucose metabolism measured with positron emission tomography after paroxetine treatment of major depression," Am. J. Psychiatry, 158(6): 899-905, 2001.

Liotti et al., "The role of functional neuroimaging in the neuropsychology of depression," J. Clin. Exp. Neuropsychol., 23(1): 121-36, 2001.

Mayberg, "Depression, II: localization of pathophysiology," Am. J. Psychiatry, 159(12): 1979, 2002.

Rauch, S. L., "Neuroimaging and Neurocircuitry Models Pertaining to the Neurosurgical Treatment of Psychiatry Disorders," Neurosurg Clin N. Am., vol. 14, 2003, pp. 213-223.

Sheline, Yvette, "3D MRI Studies of Neuroanatomic Changes in Unipolar Major Depression: The Role of Stress and Medical Comorbidity," Biol Psychiatry, vol. 48, 2000, pp. 791-800.

ISA/US Commissioner for Patents, International Search Report for PCT/US2006/041171 dated Jul. 27, 2007.

European Patent Office, Supplementary European Search Report for EP06836445 dated Feb. 19, 2009.

* cited by examiner

NEURAL STIMULATION AND OPTICAL MONITORING SYSTEMS AND METHODS

CROSS-REFERENCE TO RELATED APPLICATION

This application claims the benefit of U.S. Provisional Application No. 60/728,650, filed Oct. 19, 2005, which is incorporated herein by reference in its entirety.

TECHNICAL FIELD

The present disclosure generally relates to the use of optical monitoring techniques in association with providing neural stimulation to particular target neural populations. More particularly, the present disclosure describes various embodiments of optical monitoring systems, devices, and/or elements that may be used in association with particular neural stimulation systems, devices, and/or elements.

BACKGROUND

A wide variety of mental and physical processes are controlled or influenced by neural activity in particular regions of the brain. For example, the neural functions in some areas of the brain (i.e., the sensory or motor cortices) are organized according to physical or cognitive functions. In general, particular areas of the brain appear to have distinct functions in most individuals. In the majority of people, for example, the areas of the occipital lobes relate to vision, the regions of the left interior frontal lobes relate to language, and the regions of the cerebral cortex appear to be consistently involved with conscious awareness, memory, and intellect.

Many problems or abnormalities with body functions can be caused by dysfunction, damage, disease and/or disorders in the brain. Effectively treating such abnormalities may be very difficult. Epidemiological profiles indicate that the treatment and/or rehabilitation of neurologic dysfunction is extremely challenging due to patient population heterogeneity, for example, due to factors such as age, gender, ethnicity, cause, physiologic location, severity, and time since onset. For most patients exhibiting neurologic damage arising from, for example, a stroke, conventional treatments are not sufficient, and little can be done to significantly improve the function of an affected body part or cognitive function beyond the limited recovery that generally occurs naturally without intervention.

Optical monitoring may facilitate the evaluation of various types of tissue conditions and/or properties, for example, through near infrared spectroscopy (NIRS). A need exists for neural stimulation systems and methods that include or incorporate particular optical monitoring techniques.

DETAILED DESCRIPTION

A. Introduction

The following disclosure describes various embodiments of neural stimulation and optical monitoring (NSOM) systems. Different types of tissues or substances may absorb, transmit, scatter, reflect, and/or emit optical signals in different manners based upon the optical response characteristics of such tissue or substances. For example, optical signals may be used to detect, monitor, estimate, or measure changes in hemodynamic properties (e.g., fluctuations in oxy-hemoglobin or deoxy-hemoglobin levels, blood volume, or blood flow) and/or other tissue properties, typically in a selective manner. Irradiation of tissues or substances with optical signals having particular characteristics (e.g., single or multiple wavelengths, and/or coherent light) may facilitate the detection, identification, or measurement of specific types of biological information. Systems and methods in accordance with various embodiments of the invention may comprise devices configured for near infrared spectroscopy (NIRS), optical tomography (OT), laser Doppler flowmetry, fluorescence spectroscopy, and/or other optical techniques.

Depending upon embodiment details, systems in accordance with various embodiments of the present invention may comprise one or more types of neural stimulation devices and/or signal transfer elements configured to apply neural stimulation signals to a set of stimulation sites; and one or more types of optical signal sources, optical signal detectors, and optical signal transfer elements configured to monitor or measure optical signals and/or signal properties at a set of optical monitoring sites.

Some embodiments may apply or deliver particular types of neural stimulation and/or chemical substances to a patient in association with optical monitoring. A neural stimulation and/or chemical delivery and optical monitoring system (NSCDOMS) may comprise a set of neural stimulation devices configured to provide stimulation signals to a set of stimulation sites; one or more chemical substance infusion or delivery devices (e.g., an implantable drug infusion pump) configured to release or apply one or more chemical substances (e.g., an amphetamine, a pharmacologic agent, a neuroprotective agent, neurotrophic agent, a growth factor, a muscle relaxant, or another substance) to a set of delivery sites upon or within a patient's body; and a set of optical signal sources, detectors, and other optical elements (e.g., optical fibers).

Particular system embodiments may also include other types of monitoring systems and/or devices for monitoring or measuring patient state signals and/or patient responses, as further described below. Various system embodiments may further comprise hardware and/or software for processing or analyzing neural stimulation, chemical, optical, and/or other types of signals.

Systems and methods in accordance with various embodiments of the invention may be directed toward restoring, developing, and/or enhancing particular types of neural function, and/or treating or ameliorating neurologic dysfunction. Neurologic dysfunction may include disorders, diseases, injuries, and/or abnormalities related to brain and/or other neural tissue functions. Representative types of neurologic dysfunction may correspond to stroke, traumatic brain injury (TBI), a maladaptive neuroplastic condition, a pain syndrome, auditory disorders (e.g., tinnitus or auditory hallucinations), speech or language disorders (e.g., aphasia), learning disorders (e.g., dyslexia), Parkinson's Disease, essential tremor, and/or one or more other disorders, states or conditions.

Optical monitoring may facilitate the determination of (1) one or more neural stimulation and/or chemical substance delivery sites; (2) levels (e.g., a peak amplitude), ranges, and/or other characteristics (e.g., a pulse repetition frequency or a modulation pattern) of particular neural stimulation and/or chemical substance delivery parameters; (3) whether neural stimulation and/or a chemical substance therapy is providing an intended or desirable effect; (4) whether to initiate, query, adjust, vary, interrupt, resume, or discontinue neural stimulation and/or a chemical substance therapy, possibly in an adaptive manner; and/or (5) a likelihood that a patient will experience a given or target level of neurofunctional restoration development in association with neural stimulation and/or chemical substance therapy.

Depending upon embodiment details, neural stimulation may correspond to transcranial, cortical, subcortical, deep brain, cerebellar, spinal column, cranial or other peripheral nerve, and/or other types of neural stimulation. Representative types of neural stimulation that may be employed in particular embodiments include one or more of cortical stimulation (CS), vagal nerve stimulation (VNS), deep brain stimulation (DBS), transcranial magnetic stimulation (TMS), and transcranial direct current stimulation (tDCS).

The neural stimulation, substance delivery, and/or optical monitoring may be directed toward one or more anatomical locations. An anatomical location or region at which neural stimulation signals are applied or delivered to, or through, or near a target neural population may be defined as a stimulation site. One or more optical monitoring sites may be external or internal to a patient, and may be essentially identical or proximate or near a stimulation site; or distant or remote from a given stimulation site.

A stimulation site and/or a target neural population may be identified and/or located in a variety of manners, for example, through one or more procedures involving anatomical landmark identification; structural and/or functional anatomical imaging (e.g., Magnetic Resonance Imaging (MRI), Diffusion Tensor Imaging (DTI), functional MRI (fMRI), Positron Emission Tomography (PET), Magnetic Resonance Angiography (MRA), Near-infrared Spectroscopy (NIRS) or Optical Tomography (OT), or Magnetoencephalography (MEG)); electrophysiological signal measurement (e.g., electroencephalography (EEG) or electromyography (EMG)); anatomical spectroscopy (e.g., Magnetic Resonance Spectroscopy (MRS)); and/or other techniques. Representative manners of identifying a target neural population and/or a stimulation site are given in U.S. Pat. No. 7,010,351, which is incorporated herein by reference in its entirety.

A substance delivery site may correspond, for example, to a target neural population or a target vascular structure. A delivery site may be identified in a variety of manners, for example, through a set of procedures involving anatomical landmark identification and/or medical imaging (e.g., Magnetic Resonance Angiography (MRA)). A representative type of neural stimulation and/or chemical substance infusion system that may be applicable to particular embodiments of the invention is described in U.S. Pat. No. 6,782,292, which is incorporated herein by reference in its entirety. Those of ordinary skill in the relevant art will understand that in general, a substance delivery device may include a control unit, a substance reservoir, an implantable pump unit, and one or more substance delivery elements (e.g., a catheter). The control unit may manage the release or delivery of a substance to particular infusion sites in predetermined amounts at one or more times.

An optical monitoring site may be determined in association with the identification of a neural stimulation site (e.g., in a manner that corresponds to a type of neural activity measured by fMRI), a substance delivery site, and/or the identification of other anatomical sites of interest, for example, particular vascular structures and/or certain types of neural tissue. Such neural tissue may comprise, for example, neural populations within, proximate to, or having projections associated with a lesion or an infarct penumbra; neoplastic tissue; vascular structures; and/or implanted cells (e.g., at least partially undifferentiated cells such as stem cells). In some embodiments, one or more optical monitoring sites may be associated with multiple brain regions in accordance with a known or standard type of optical monitoring system or device configuration, which may facilitate the acquisition and analysis of optical signals corresponding to a variety of neural functions.

In various embodiments, the neural stimulation device(s) may apply or deliver stimulation signals to a patient, which may comprise electromagnetic, acoustic, thermal, and/or other types of signals (e.g., mechanical forces) capable of affecting neural function. Electromagnetic stimulation signals may be defined in accordance with spatial, temporal, electrical, and/or magnetic signal parameters, properties and/or characteristics. Such stimulation signals may take on various forms, and may be characterized by various waveform characteristics (e.g., signal amplitude, duration, duty cycle, polarity, pulse width, phase information, pulse repetition frequency, and burst frequency). Spatial, temporal, and/or waveform parameters may be varied in one or more manners to enhance a likelihood of providing, maintaining, or prolonging symptomatic relief from neurologic dysfunction.

Neural stimulation signals and/or chemical substances may be applied to the patient in association an adjunctive therapy such as a behavioral therapy, which may comprise one or more of physical therapy; physical and/or cognitive skills training or practice, such as training in Activities of Daily Living (ADL); intentional use of an affected body part; speech therapy; vision, visual, and/or spatial perception training; a reading task; a writing task; an auditory activity, for example, a musical or rhythmic task or training; attention tasks; a cognitive activity, memory task, or memory training; comprehension tasks; and/or other therapies or activities.

Optical signals may be monitored and/or analyzed before, during, and/or after the application of neural stimulation signals and/or chemical substances to the patient. In certain embodiments, based upon particular types of optical signal properties and/or changes therein, the application of neural stimulation signals and/or chemical substances may be initiated, queried, adjusted, interrupted, resumed, and/or discontinued, possibly in an adaptive or generally adaptive manner, which may occur on a real time, near-real time, or delayed basis.

Figure 1:
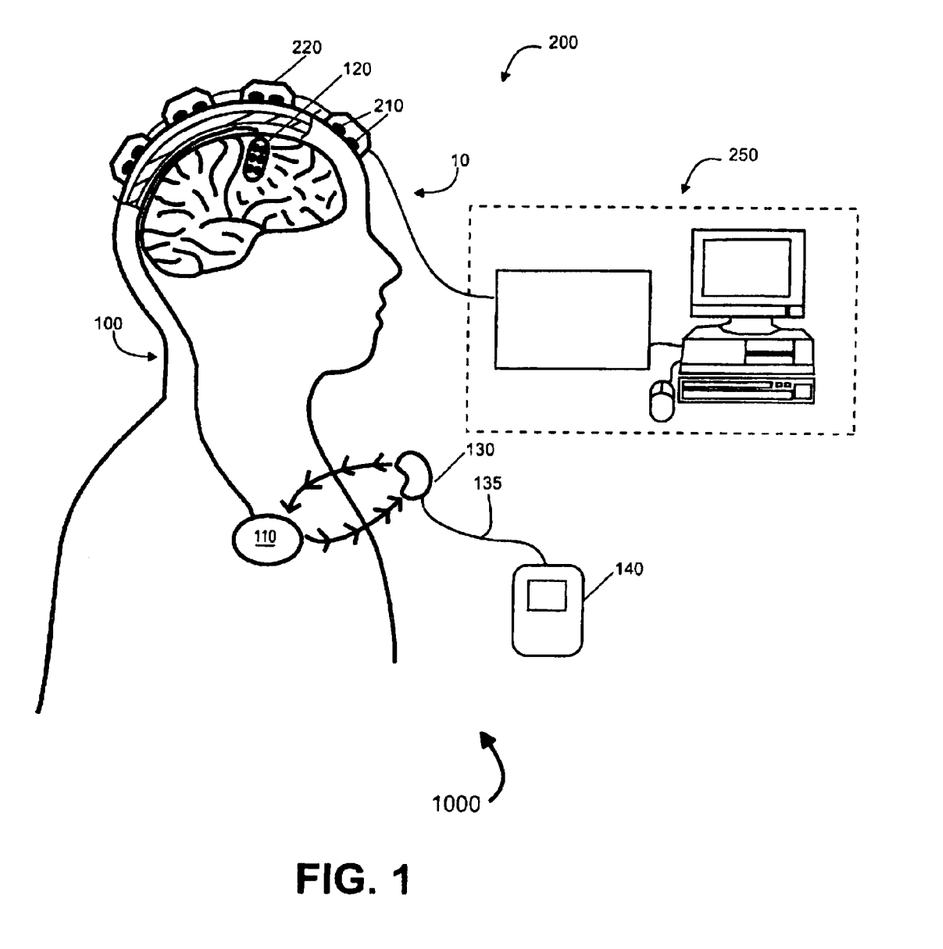
FIG. 1 is a schematic illustration of a neural stimulation and optical monitoring system configured in accordance with an embodiment of the invention.

B. Embodiments of Neural Stimulation and Optical Monitoring Systems and Methods for Using Such Systems FIG. 1 is a schematic illustration of a neural stimulation and optical monitoring (NSOM) system 1000 according to an embodiment of the invention. In one embodiment, the NSOM system 1000 comprises a neural stimulation system (NSS) 100 and an external optical monitoring system 200. The NSS 100 may comprise an implantable pulse generator (IPG) 110 that is coupled to a set of implanted signal transfer devices, electrode assemblies, and/or electrodes 120. The NSS 100 may also comprise one or more types of signal or substance monitoring devices, for example, an electrode assembly configured to monitor electrocorticographic (ECoG) signals. Depending upon embodiment details, the NSS 100 may comprise fully implanted components that are surgically placed within a patient 10, as illustrated; and/or components that are partially implanted or external to the patient 10.

The NSS 100 may further comprise an external programming or communication device 130, which in some embodiments facilitates unidirectional or bi-directional signal transfer (e.g., through magnetic or RF telemetry) involving the IPG 110. Such communication may involve the transfer of configuration information, program instructions, stimulation signal parameters, power signals, and/or data. The communication device 130 may be coupled to a programming device 140 (e.g., a personal digital assistant (PDA) or a handheld, laptop, or desktop computer) by a wire-based or a wireless link 135.

An optical monitoring system 200 may comprise a system for applying optical signals to and detecting optical signals scattered within or reflected by living tissue. Such a system may involve near infrared spectroscopy or optical topography. In one embodiment, the optical monitoring system 200 comprises at least one optical source/detector pair 210 carried by a monitoring structure 220; and a control/analysis unit 250. Some embodiments may comprise multiple source/detector pairs 210 carried by a single or multiple monitoring structures 220. In certain embodiments the optical monitoring system 200 may be configured for wireless or wire-based signal transfer with the programming device 140; or the communication device 130 may be coupled to the optical monitoring system 200 in an embodiment that omits the programming device 140. In a representative embodiment, the optical monitoring system 200 comprises an imagent™ functional brain imaging system and/or an OxiplexTS™ tissue oximeter, both of which are commercially available from ISS, Inc., of Champaign, Ill.

Figure 2:
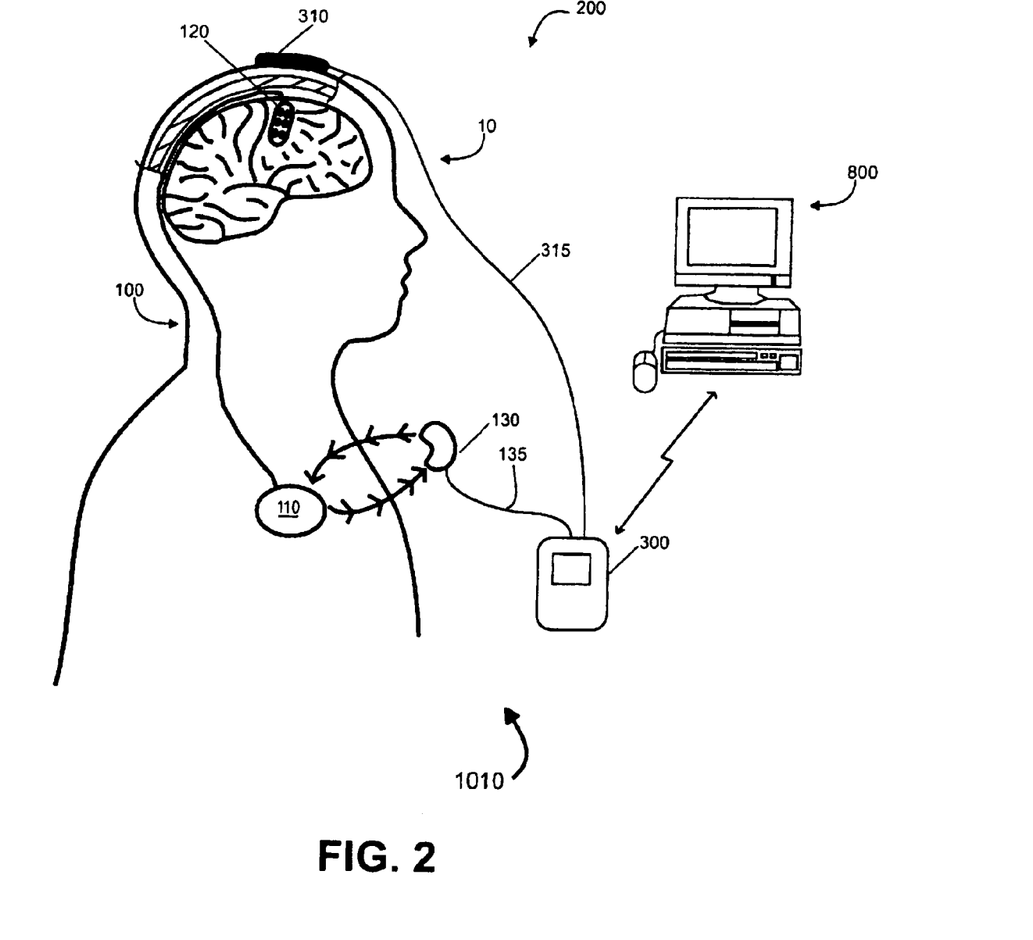
FIG. 2 is a schematic illustration of a neural stimulation and optical monitoring system configured in accordance with another embodiment of the invention.

FIG. 2 is a schematic illustration of an NSOM system 1010 according to an embodiment of the invention. In one embodiment, the NSOM system 1010 comprises an IPG 110; a set of electrode assembles or electrode devices 120 configured to receive and apply neural stimulation signals; a communication device 120; an optical monitoring assembly 310; and an optical monitoring and programming device (OMPD) 300. In some embodiments, an IPG 110 may be implanted at an above-neck location rather than at a subclavicular location as shown in FIGS. 1 and 2.

The communication device 130 may be configured for wireless signal transfer to and/or from the IPG 110, and may be coupled to or carried by the OPMD 300. In one embodiment, the communication device 130 is coupled to the OPMD 300 by a link 135. The optical monitoring assembly 310 may be configured for monitoring optical signals at one or more external locations on the patient's anatomy, and may be configured for wireless or wire-based communication with the OPMD 300. In one embodiment, the optical monitoring assembly 310 may be coupled to the OPMD 300 by a link 315.

The optical monitoring assembly 310 may comprise a set of optical sources, a set of optical detectors, and electrical and/or optical signal transfer elements, for example, in a manner described in detail by Alper Bozkurt et al. in "A portable near infrared spectroscopy system for bedside monitoring of newborn brain," *BioMedical Engineering Online* 2005, 4:29, which is incorporated herein by reference in its entirety. The optical sources and detectors may be carried by one or more support members 312, which may be positioned at desired monitoring locations (e.g., upon a patient's head or scalp).

The OPMD 300 comprises a device such as a PDA or a handheld, laptop, or desktop computer having hardware and software configured to (1) direct the generation and detection of optical signals; (2) process and/or analyze the detected signals; (3) visually indicate (e.g., by way of a display device and/or a graphical user interface) detected, estimated, or measured optical signal properties and/or physiologic or physiologic correlate properties associated therewith; (4) direct the specification or selection of neural stimulation parameters, which may include waveform, spatial, and/or temporal parameters; and/or (5) communicate with the IPG 110 to facilitate or effectuate the transfer or exchange of neural stimulation parameters and/or other information (e.g., patient data; or measured, sampled, or stored ECoG signals).

The optical monitoring, signal processing, and/or information presentation functionality of the OPMD 300 may be implemented in a manner that is essentially identical, analogous, or similar to that described by Bozkurt et al. In some embodiments, the OPMD 300 may be configured for wireless or wire-based communication with a computer system 800 to facilitate certain types of signal processing, analysis, and/or characterization operations. In certain embodiments, the communication device 130 and the optical monitoring assembly 310 may be integrated into or carried by a single housing or structure, which may be handheld or adapted for wearing or carrying by the patient 10.

Figure 3:
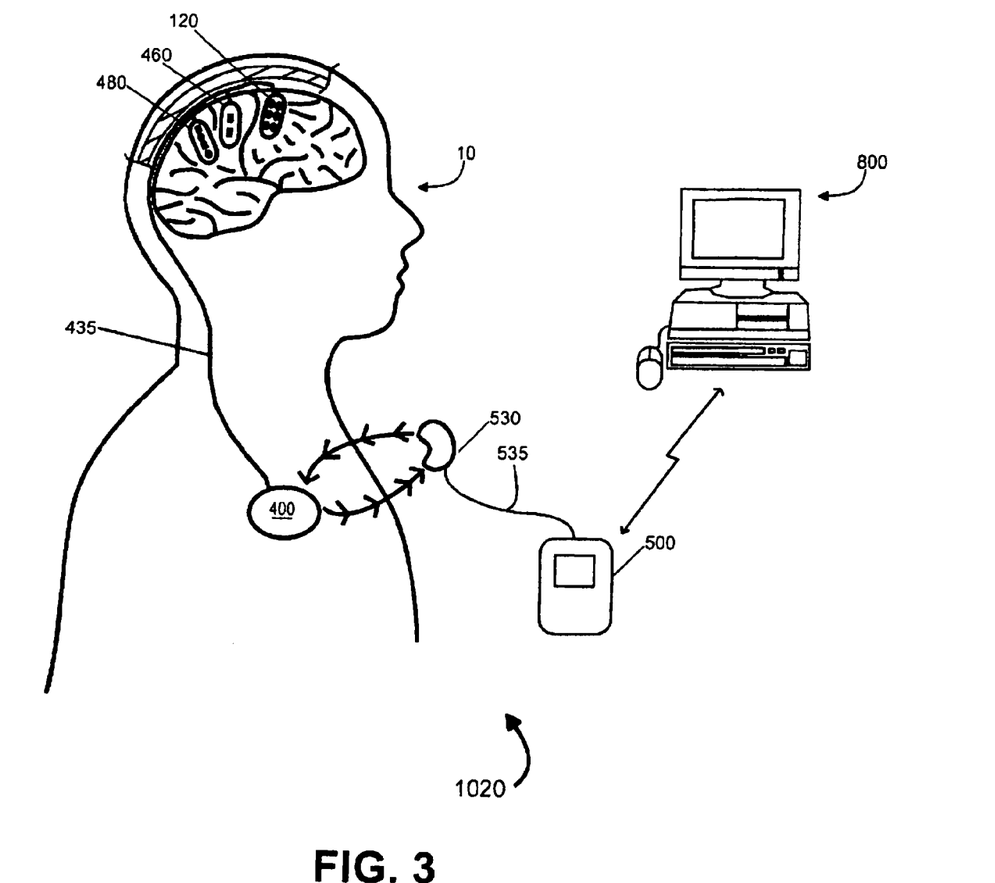
FIG. 3 is a schematic illustration of a neural stimulation and optical monitoring system configured in accordance with still another embodiment of the invention.

FIG. 3 is a schematic illustration of an NSOM system 1020 according to another embodiment of the invention. In one embodiment, the NSOM system 1020 comprises an implantable stimulation and optical monitoring controller (ISOMC) 400 that is coupled to a set of electrode assemblies or devices 120, a set of optical monitoring assemblies (OMAs) 460, and/or a set of stimulation and optical monitoring assemblies (SOMAs) 480 by way of one or more links 435. Depending upon a type of device under consideration, a link 435 may comprise one or more lead wires and/or optical fibers to provide pathways for electrical and optical signals. An electrode assembly 120 may be implanted epidurally or subdurally. Depending upon embodiment details, an OMA 460 or a SOMA 480 may be implanted subcutaneously, epidurally, or subdurally.

In some embodiments, multiple OMAs 460 and/or SOMAs 480 may be implanted at or relative to different, possibly distant, brain locations. Such brain locations may be in the same or different brain hemispheres, such that noise or certain types of background activity that may affect detected optical signal properties may be subtracted from or otherwise compensated for relative to signals detected by particular OMAs 460 and/or SOMAs 480 under consideration with respect to desired brain locations.

Additionally or alternatively, optical signals detected in association with an OMA 460 and/or a SOMA 480 implanted relative to a first brain location may be used to (1) determine whether to apply, modify, or discontinue neural stimulation in a different brain area, and/or (2) select or identify one or more neural stimulation parameters in accordance with which neural stimulation will be applied in a different brain area. For example, in a representative embodiment, one OMA 460 may detect particular hemodynamic properties associated with neural activity in a healthy brain region, while another OMA 460 or a SOMA 480 detects hemodynamic properties associated with neural activity in a homologous brain region that exhibits a type of neurologic dysfunction, for example, a maladaptive neuroplastic condition (e.g., tinnitus or a central pain syndrome). Based upon a difference or relationship between detected optical signals corresponding to such brain regions, the application of neural stimulation signals to the brain region exhibiting neurologic dysfunction may be initiated, continued, varied, interrupted, resumed, or discontinued.

The NSOM system 1020 further comprises a communication device 530 that is configured for wireless or wire-based signal transfer with an external stimulation and optical monitoring programming device (SOMPD) 500. The communication device 530 may be coupled to the SOMPD 500 by a link 535. The communication device 530 is also configured for wireless communication with the ISOMC 400, such that neural stimulation parameters, optical monitoring parameters, and optical monitoring signals or results may be communicated between the SOMPD 500 and the ISOMC 400.

In various embodiments, the SOMPD 500 may (1) direct the selection of neural stimulation and/or optical monitoring instructions, commands, and/or parameters, and their issuance to the ISOMC 400; (2) receive, process, and/or analyze signals or information received from the ISOMC 400; (3) visually indicate neural stimulation information; (4) visually indicate detected, estimated, or measured optical signal properties and/or physiologic or physiologic correlate properties associated therewith; and/or (5) perform different or additional functions. Depending upon embodiment details, the SOMPD 500 may comprise a PDA or a handheld or other type of computer. Particular signal processing and/or information presentation functionality provided by the SOPMD 500 may be implemented in a manner that is essentially identical, analogous, or similar to that described above with respect to the OPMD 300.

Figure 4:
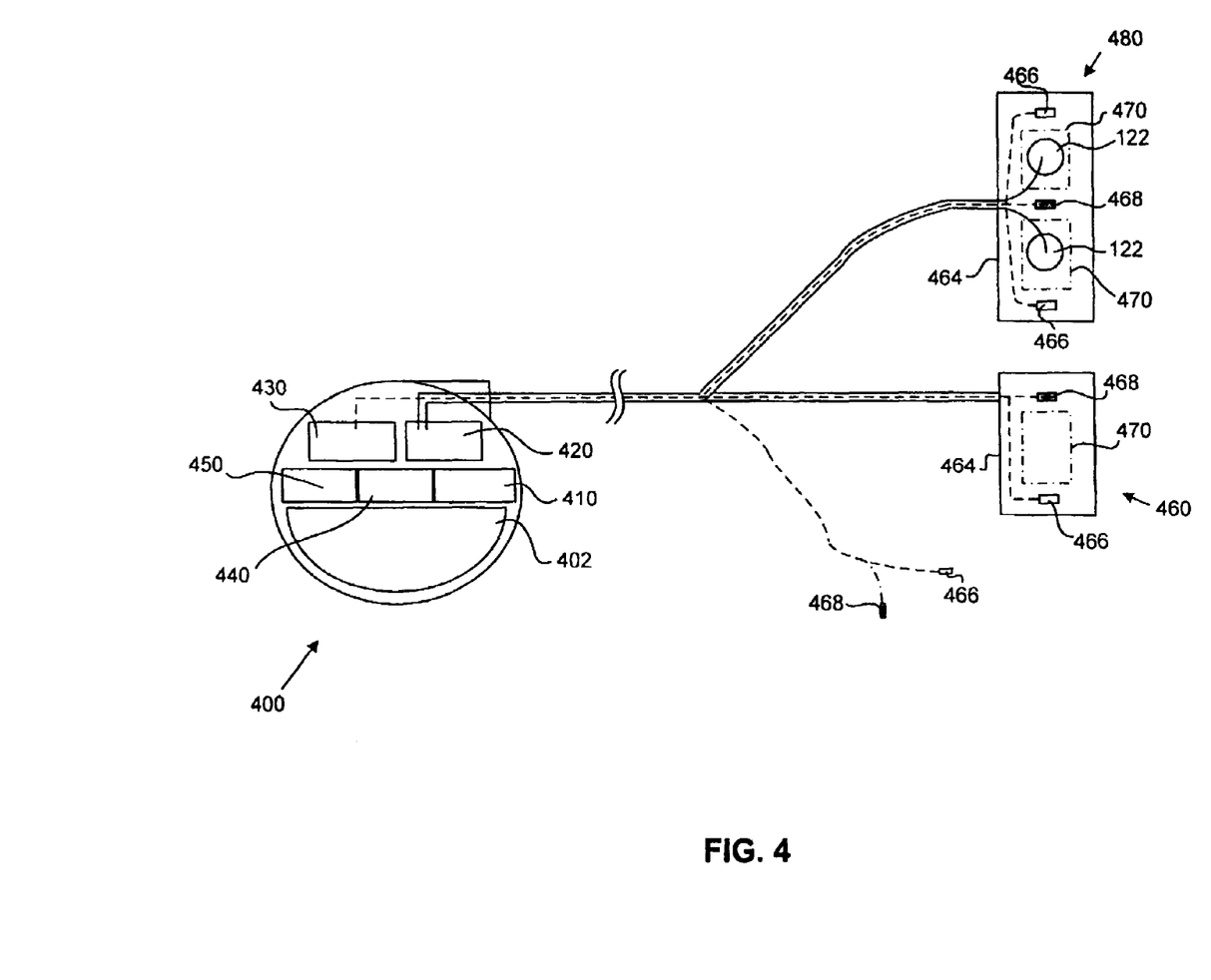
FIG. 4 is a schematic illustration of an implantable stimulation and optical controller that may be coupled to an electrode assembly, an optical monitoring assembly, and/or a stimulation and optical monitoring assembly according to an embodiment of the invention.

FIG. 4 is a schematic illustration of an ISOMC 400 that may be coupled to an electrode assembly 120, an OMA 460, and/or a SOMA 480, and/or individual light emitting and/or light detecting devices (e.g., individual fibers or a set of fibers, which may possibly have microlens, wavelength filtering, and/or light directing elements coupled thereto) according to an embodiment of the invention. In one embodiment, the ISOMC 400 comprises a power source 402, a pulse generator 410, an electrical signal I/O unit 420, an optical signal input/output (I/O) unit 430, a signal processing unit 440, and a control and communication unit 450. The power source 402 may comprise a battery, a capacitor, and/or another type of energy storage device. The power source 402 may be rechargeable in certain embodiments. The pulse generator 410 may comprise circuitry for generating and outputting neural stimulation signals in accordance with spatial, temporal, and/or waveform parameters.

The electrical signal I/O unit 420 may comprise circuitry for interfacing electrical signal transfer elements such as lead wires, electrical contacts or electrodes, electrode devices, and/or electrode assemblies 120 to (1) the pulse generator 410; (2) signal storage elements, such as an electronically writable, configurable, or programmable medium; and/or (3) the signal processing unit 440 in a manner understood by those skilled in the art.

The optical signal I/O unit 430 may comprise one or more types of light emitting and light detecting devices, which may include one or more of a light emitting diode (LED), a semiconductor laser, and a photodetector. The optical signal I/O unit 430 may additionally comprise one or more types of optical elements such as wavelength filters, beam splitters, electrical and/or optical multiplexors, and/or micromechanical optical switches. Additionally, the optical signals I/O unit 430 may comprise particular types of signal modulation elements, in a manner understood by those skilled in the art.

In various embodiments, the optical signal I/O unit 430 may include multiple light emitting devices, each of which is configured to generate light centered at a particular wavelength and/or having a desired bandwidth. The optical signal I/O unit may also include multiple light detecting devices in a corresponding manner. Depending upon embodiment details, the optical signal I/O unit 430 may activate subsets of sources and detectors at one or more times (e.g., in a time multiplexed manner), which may facilitate power conservation. In certain embodiments, NIRS may be facilitated by multiple infrared LEDs or semiconductor lasers operating at optical wavelengths that may be particularly affected by hemodynamic properties. In an alternate embodiment, light emitting devices (e.g., LEDs) may output light in the ultraviolet (UV) spectrum to facilitate fluorescence spectroscopy measurements (e.g., based upon wavelength dependent fluorescence intensity differences exhibited by different tissue types, such as healthy tissue versus neoplastic tissue).

One representative type of device that may be suitable for particular embodiments of the ISOMC 400 is described by Eiji Higurashi et al., in "An Integrated Laser Blood Flowmeter," *Journal of Lightwave Technology*, Vol. 21, No. 3, March 2003, which is incorporated herein by reference in its entirety. Another type of device that may be suitable for particular ISOMC embodiments is described by S. Shinohara et al., in "Laser Doppler velocimeter using the self-mixing effect of a semiconductor laser diode," *Applied Optics*, Vol. 25, No. 9, p. 1417-1419, May 1986, which is incorporated herein by reference in its entirety.

The signal processing unit 440 may comprise an analog and/or digital signal processing device for performing operations such as signal filtering; noise compensation; mathematical operations and/or signal analysis associated with intensity, power, spectral, and/or phase characteristics of detected optical signals; and/or other operations that may involve generated and/or detected optical signals (e.g., monitoring self-mixing behavior.

The control and communication unit 450 may comprise (1) a processing unit and associated circuitry for directing or managing the application of neural stimulation signals and the detection and processing of optical signals, and (2) telemetric communication circuitry that directs or manages signal transfer with the communication device 530. Such signal transfer may involve the transfer of measured or processed optical monitoring signals, such that they may be analyzed by an external device (e.g., the SOMPD 500 or other device).

In some embodiments, optical monitoring operations may occur on a periodic, intermittent, or specifically requested basis in order to conserve power. In some embodiments, the control and communication unit 450, the SOMPD 500, and/or another device may determine one or more neural stimulation parameters based upon detected and/or processed optical signals, and possibly initiate, adjust, vary, query, interrupt, resume, or discontinue the application of neural stimulation signals based upon such detected or processed signals.

In certain embodiments, an ISOMC 400 may comprise, be based upon, and/or utilize one or more elements described in U.S. Pat. Nos. 5,520,190 and 5,601,611, both of which are incorporated herein by reference in their entireties.

Also shown in FIG. 4 is an OMA 460 according to an embodiment of the invention. In one embodiment, the OMA 460 comprises a support member or structure 464 configured to carry a set of optical emission elements 466 and a set of optical detection elements 468. In various embodiments, an optical emission element 466 and/or an optical detection element 468 may comprise a set of optical fibers, possibly coupled to a lens or microlens; a wavelength filter; and/or another type of optical signaling element (e.g., a MEMS device). The optical fibers may be coupled to the optical I/O unit 430. In some embodiments, one or more portions of the support member or structure 464 may carry blocking, shielding, or filtering elements (e.g., an optically opaque, absorbing, or blocking material, coating, or layer) through which undesirable optical signals (e.g., optical signals originating external to the patient 10) that may affect optical monitoring operations.

The emission and detection elements 466, 468 may be positioned relative to each other in a manner that facilitates the detection of optical signals that are scattered, reflected, and/or emitted (e.g., in association with fluorescence) by target tissues, which may reside proximate to and/or somewhat distant from a monitoring site. In a representative embodiment, particular emission and detection elements 466, 468 may be separated from each other by approximately 0.5 cm to approximately 5.0 cm, or approximately 1.5 cm to approximately 3.5 cm, or approximately 2.0 cm to 3.0 cm.

Depending upon embodiment details and/or particular target tissues under consideration, optical signals detected by an OMA 460 may correspond or generally correspond to a target monitoring region 470. A target monitoring region 470 may be defined or approximately defined based upon a type of optical signal path through tissue, which may correspond to a modified Beer-Lambert law. In a representative embodiment, an OMA 460 may be implemented in a manner analogous to that described in U.S. Pat. No. 5,024,226, which is incorporated herein by reference in its entirety.

Figure 5:
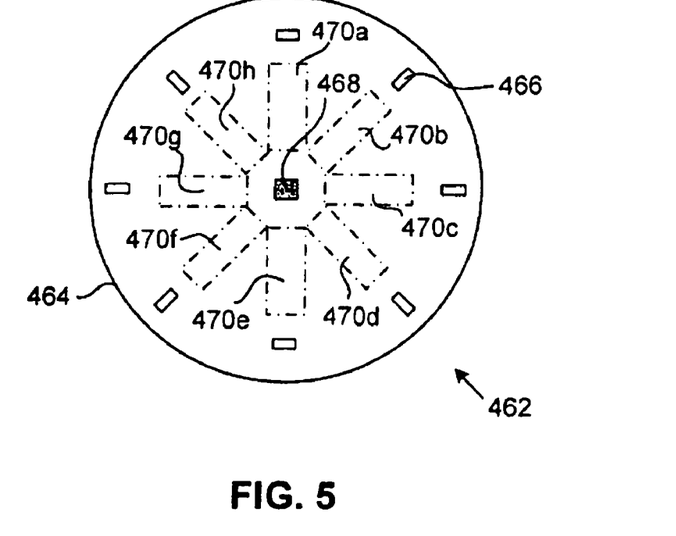
FIG. 5 is a schematic illustration of an optical monitoring assembly configured in accordance with an embodiment of the invention.

FIG. 5 is a schematic illustration of an OMA 462 according to another embodiment of the invention. The OMA 462 of FIG. 5 comprises emission elements 466 and detection elements 468 exhibiting a different configuration than that shown in FIG. 4, and which may facilitate monitoring corresponding to multiple target monitoring regions 470*a-h*.

Also shown in FIG. 4 is a SOMA 480 according to an embodiment of the invention. In one embodiment, the SOMA 480 comprises a support member or structure 464 configured to carry a set of electrical contacts or electrodes 122, a set of optical emission elements 466, and a set of optical detection elements 468. The electrodes 122 may be coupled to the electrical signal I/O unit 420 by a set of lead wires 124, and the optical emission and detection elements 466, 468 may be coupled to the optical signal I/O unit 430. A target monitoring region 470 may correspond to tissue located between, beneath, and/or proximate to one or more electrodes 122.

Figure 6A:
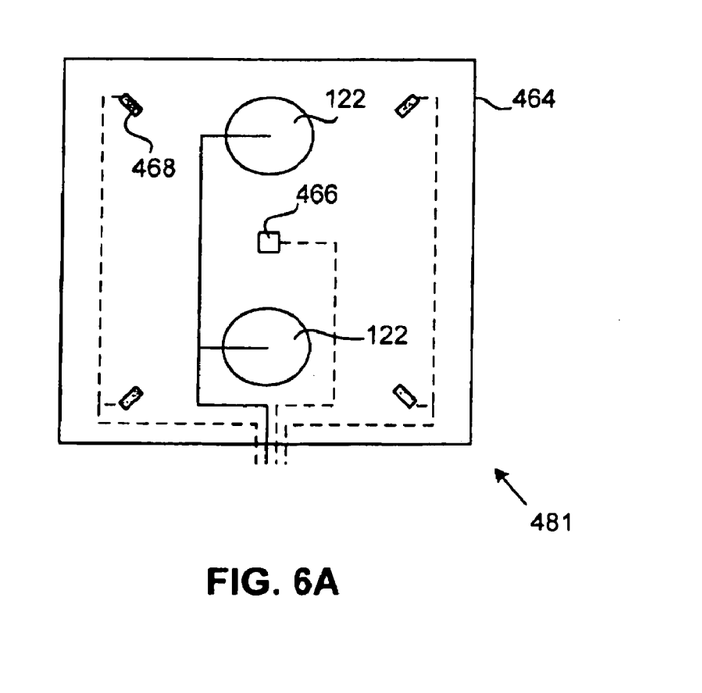
FIG. 6A is a schematic illustration of a stimulation and optical monitoring assembly configured in accordance with an embodiment of the invention.

FIG. 6A is a schematic illustration of a SOMA 481 according to another embodiment of the invention. In one embodiment, the SOMA 481 comprises a set of electrodes 122, optical emission elements 466, and optical detection elements 468 configured in a manner that establishes or approximately establishes one or more optical signal phase relationships between emission and detection elements 466, 468. For instance, a set of optical emission elements 466 and a set of optical detection elements 468 may be positioned, organized, or arranged to form a phased optical array. Such phase relationships may be relevant to phase cancellation optical signal analysis as described by Britton Chance et al., in "A novel method for fast imaging of brain function, non-invasively, with light," *Optics Express*, Vol. 2, No. 10, 11 May 1998, p. 411-423, which is incorporated herein by reference in its entirety.

Figure 6B:
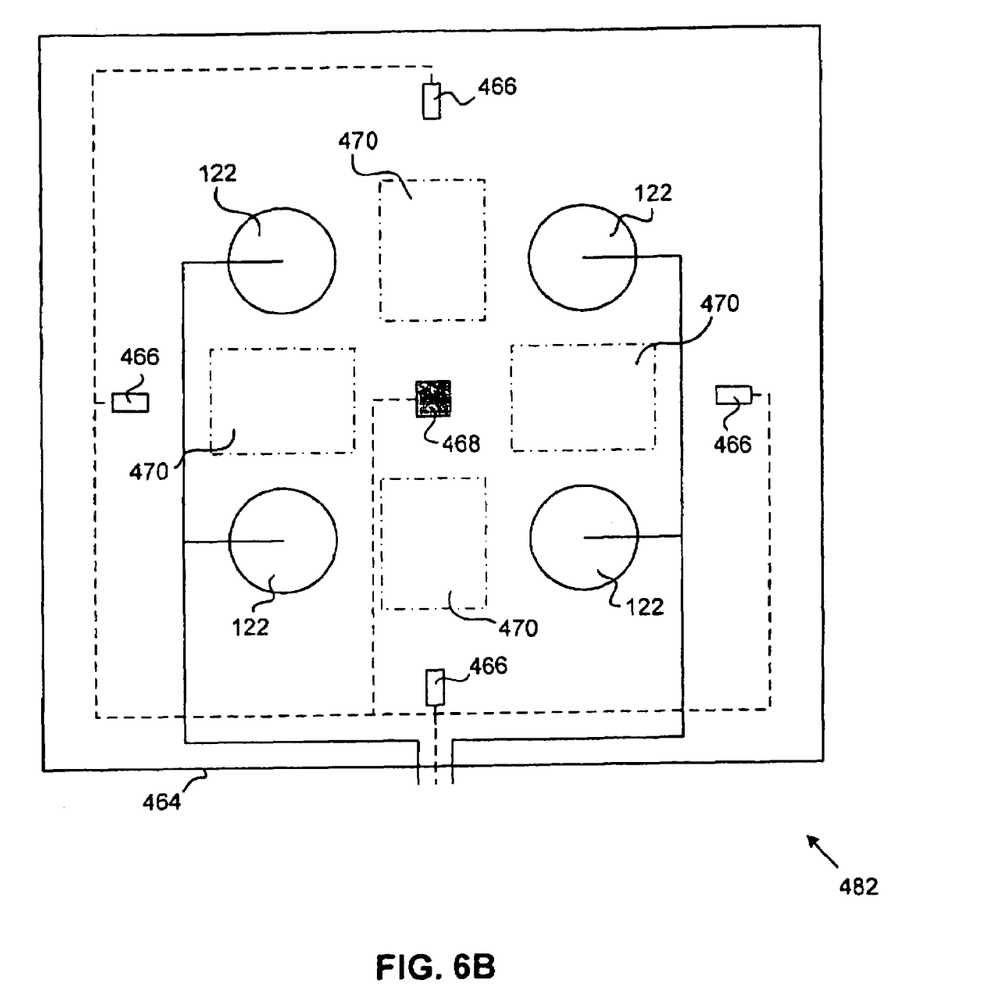
FIG. 6B is a schematic illustration of a stimulation and optical monitoring assembly configured in accordance with still another embodiment of the invention.

FIG. 6B is a schematic illustration of a SOMA 482 according to another embodiment of the invention. In one embodiment, the SOMA 482 comprises a set of electrodes 122, optical emission elements 466, and optical detection elements 468 configured in a manner that establishes multiple target monitoring regions 470. Many other types of support member, electrode, emission element, and/or detection element configurations are possible in accordance with various embodiments of the present invention.

In some embodiments, a SOMA 480, 481, 482 may omit one or more optical detection elements 468, such that optical signals output by particular optical emission elements 466 carried by the SOMA may be detected by one or more optical signal detection devices that are external to the patient (e.g., proximate to the patient's skull).

In certain embodiments, an ISOMC 400, an electrode assembly 120, an OMA 460, and/or a SOMA 480 may be implemented using peg- or screw-type structures, for example, in a manner that is identical and/or analogous to that described in U.S. patent application Publication No. US 2005/0075680, incorporated herein by reference in its entirety, and U.S. Pat. No. 5,024,226.

Figure 7:
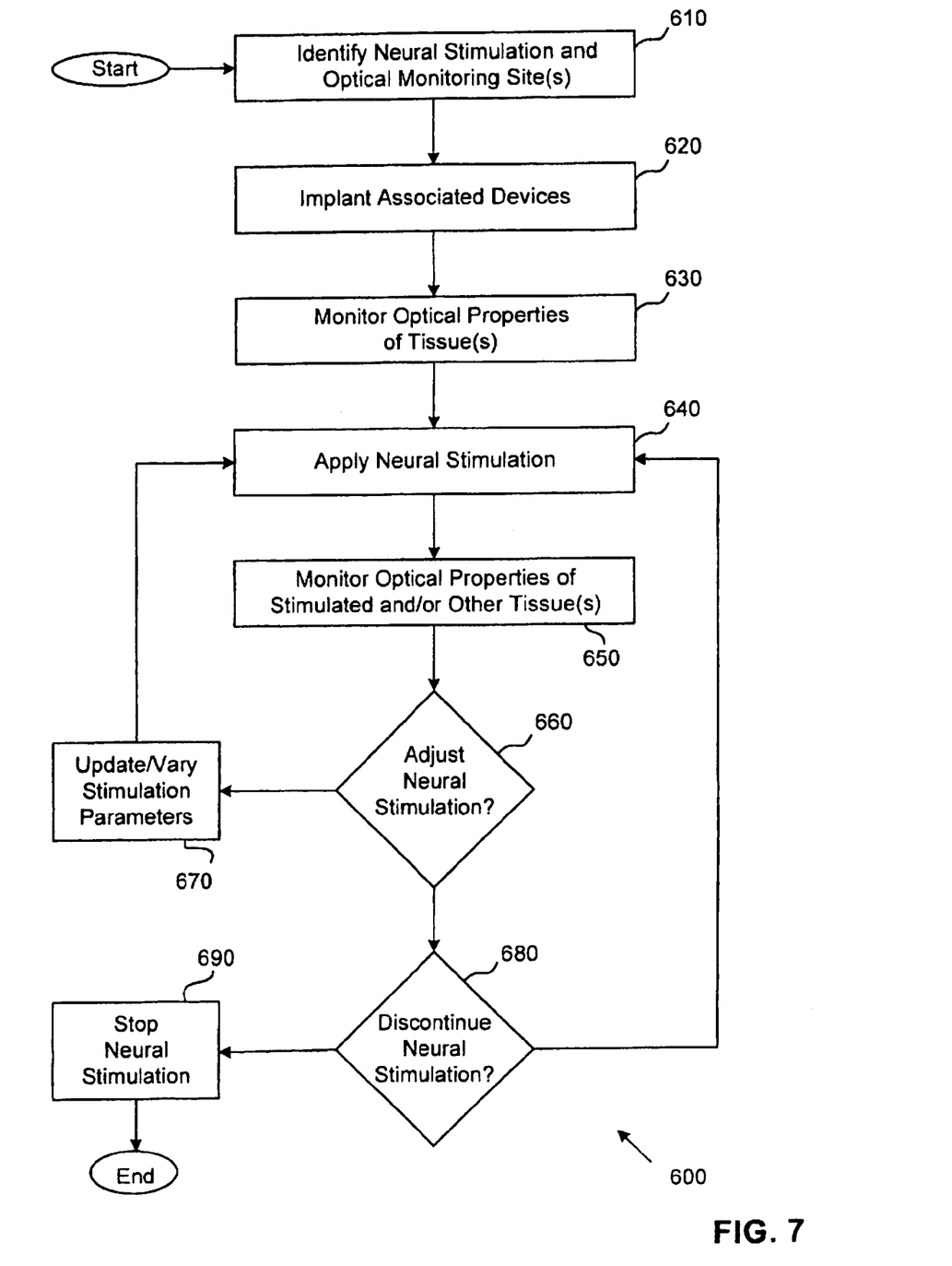
FIG. 7 is a flow diagram illustrating a process for applying neural stimulation in accordance with an embodiment of the invention.

FIG. 7 is a flow diagram of a process 600 for neural stimulation in association with optical monitoring according to an embodiment of the invention. Process 600 may contain various process portions, particular aspects of which are described in detail hereafter.

Process portion 610 can include identifying one or more neural stimulation and/or optical monitoring sites, and process portion 620 can include implanting a set of neural stimulation and possibly optical monitoring devices in a patient 10. Process portion 630 can include monitoring optical signals in patient tissue, for example, within or relative to one or more brain regions. Process portion 640 can include applying neural stimulation to the patient at one or more stimulation sites, in accordance with particular neural stimulation parameters. Process portion 650 can include monitoring optical signals in patient tissue, some of which may have been exposed to or affected by neural stimulation signals.

Process portion 660 can include determining whether to adjust or vary neural stimulation, possibly based upon particular optical monitoring signals and/or processed information associated therewith. In the event that neural stimulation is to be adjusted or modified, process portion 670 can include determining an adjusted, modified, or updated set of stimulation parameters, possibly based upon particular optical monitoring signals and/or processed information associated therewith. Process portion 640 may subsequently apply neural stimulation in accordance with the updated stimulation parameters. Adjustment of neural stimulation parameters populations may occur in a real-time, approximately real-time, or delayed manner. Process portion 680 can include determining whether to interrupt or discontinue neural stimulation, in which case process portion 690 can include discontinuing neural stimulation and possibly optical monitoring operations.

In other embodiments, a process 600 may be directed toward neural stimulation and/or chemical substance delivery in association with optical monitoring. One or more of the previously described process portions may involve the application, variation, interruption, or cessation of chemical substance delivery based upon monitored optical signals and/or processed information generated from such signals, in a manner that may or may not depend upon the application of neural stimulation to one or more target neural populations.

From the foregoing, it will be appreciated that specific embodiments of the invention have been described herein for purposes of illustration, but that various modifications may be made without deviating from the invention. For example, certain aspects of the systems and methods described above may be automated or partially automated, and may be implemented on computer systems and/or via computer-readable media. In particular embodiments, aspects of the stimulation site selection procedure and/or the evaluation procedure can be automated in such a fashion. Further, in some embodiments, data obtained from a first neural population can be used to identify signal delivery parameters for a second neural population of the same patient. In other embodiments, data obtained from stimulating one type of neural population in one patient can be used to at least influence the choice of signal delivery parameters selected for a different type of neural population in a different patient. Aspects of the invention described in the context of particular embodiments may be combined or eliminated in other embodiments. Although advantages associated with certain embodiments of the invention have been described in the context of those embodiments, other embodiments may also exhibit such advantages. Additionally, none of the foregoing embodiments need necessarily exhibit such advantages to fall within the scope of the invention. Accordingly, the invention is not limited except as by the appended claims.

I claim:

1. An apparatus for treating a neural condition, comprising:
   a signal delivery device configured to be implanted into a patient proximate to a skull of the patient and positioned to apply electromagnetic signals to one or more target neural sites within the patient;
   an implantable optical monitoring assembly configured to monitor optical properties at one or more optical monitoring sites within the patient, wherein the signal delivery device and optical monitoring assembly are both carried by an implantable, generally planar support member;
   a controller configured to be implanted into the patient, the controller being operatively coupled to the signal delivery device and the optical monitoring assembly and programmed to control both the signal delivery device and the optical monitoring assembly, and wherein the controller includes a power source to power both the signal delivery device and the optical monitoring assembly;
   the optical monitoring assembly including one or more optical emission elements carried by the support member, and one or more optical detection elements carried by the support member, wherein the one or more optical emission elements and the one or more optical detection elements are arranged relative to each other to detect optical signals from the one or more optical monitoring sites; and
   wherein the one or more optical detection elements and the one or more optical emission elements are separated from each other by approximately 0.5 cm to approximately 5.0 cm and further wherein the one or more optical detection elements are arranged in a phased optical array.

2. An apparatus for treating a neural condition, comprising:
   a substance delivery device configured to release or apply one or more chemical substances to one or more corresponding target sites upon or within a patient;
   an implantable optical monitoring assembly configured to monitor optical properties at one or more optical monitoring sites within or proximate to the skull of the patient, wherein the optical monitoring assembly is carried by an implantable, generally planar support member, and further wherein the optical monitoring assembly includes a plurality of optical emission elements arranged in a phased optical array; and
   a controller configured to be implanted into the patient, the controller being operatively coupled to the substance delivery device and the optical monitoring assembly and programmed to control both the substance delivery device and the optical monitoring assembly.

3. A method for treating a patient, comprising:
   affecting a target neural population of a patient by providing to the patient one or more chemical substances;
   detecting at least one optical signal in tissue at or proximate to one or more brain regions of the patient after providing the one or more chemical substances, wherein the optical signal is detected with an optical monitoring assembly carried by an implantable, generally planar support member, and further wherein the optical monitoring assembly includes a plurality of optical emission elements arranged in a phased optical array; and
   based on the detected optical signal, controlling at least one substance delivery parameter in accordance with which the one or more chemical substances are provided.

* * * * *